(12) United States Patent
Wilson et al.

(10) Patent No.: US 9,996,666 B1
(45) Date of Patent: *Jun. 12, 2018

(54) PHYSICIAN SCHEDULING SYSTEMS FOR MATCHING MEDICAL PROVIDERS AND PATIENTS

(71) Applicant: MD Insider, Inc., Santa Monica, CA (US)

(72) Inventors: Eric Wilson, Los Angeles, CA (US); Paul Michael White, Orinda, CA (US); Sanjay Anand, Los Angeles, CA (US); Kingshuk Chatterjee, Los Angeles, CA (US); David Norris, Malibu, CA (US)

(73) Assignee: MD Insider, Inc., Santa Monica, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/274,114

(22) Filed: Sep. 23, 2016

Related U.S. Application Data

(63) Continuation-in-part of application No. 14/482,921, filed on Sep. 10, 2014.

(Continued)

(51) Int. Cl.
*G06Q 50/24* (2012.01)
*G06F 19/00* (2018.01)
(Continued)

(52) U.S. Cl.
CPC ........ *G06F 19/327* (2013.01); *G06F 17/3053* (2013.01); *G06F 17/3087* (2013.01); *G06F 17/30867* (2013.01); *G06F 19/325* (2013.01); *G06F 19/328* (2013.01); *G06Q 10/1095* (2013.01)

(58) Field of Classification Search
CPC .. G06Q 50/24; G06Q 10/06311; G06Q 50/22; G06F 19/328; G06F 19/322; G06F 19/327; G06F 19/3431; G06F 19/345; G06F 19/363
See application file for complete search history.

(56) References Cited

U.S. PATENT DOCUMENTS

2008/0133290 A1* 6/2008 Siegrist ................ G06Q 50/22 705/2
2013/0197957 A1* 8/2013 Nudd ............... G06Q 10/06311 705/7.14

* cited by examiner

*Primary Examiner* — Maroun P Kanaan
(74) *Attorney, Agent, or Firm* — Baker Botts L.L.P.

(57) ABSTRACT

In one embodiment, a matching-engine system may receive a set of physician-selection parameters from an administrator. The physician-selection parameters may comprise a range of acceptable performance-scores and experience-scores for physicians. The matching-engine system may receive, from a user, a search query comprising a geographic location of the user, a preferred date and time for an appointment, and a user-specified symptom or a user-specified treatment. A first set of physicians may be determined based on a geographic location of each physician, a performance-score associated with the physician with respect to a base-concept associated with the search query, and an experience-score associated with the physician with respect to the base-concept. A second set of physicians is identified from the first set based on one or more physician preferences, the preferred date and time, and an indication of whether the physician is available at the preferred date and time.

17 Claims, 27 Drawing Sheets

Related U.S. Application Data

(60) Provisional application No. 62/222,329, filed on Sep. 23, 2015, provisional application No. 61/876,105, filed on Sep. 10, 2013.

(51) Int. Cl.
*G06Q 10/10* (2012.01)
*G06F 17/30* (2006.01)

PHYSICIAN SCHEDULING SYSTEMS FOR MATCHING MEDICAL PROVIDERS AND PATIENTS

PRIORITY

This application claims the benefit, under 35 U.S.C. § 119(e), of U.S. Provisional Patent Application No. 62/222,329, filed 23 Sep. 2015, which is incorporated herein by reference. This application is also a continuation-in-part under 35 U.S.C. § 120 of U.S. patent application Ser. No. 14/482,921, filed 10 Sep. 2014, which claims the benefit, under 35 U.S.C. § 119(e), of U.S. Provisional Patent Application No. 61/876,105, filed 10 Sep. 2013, each of which is incorporated herein by reference.

TECHNICAL FIELD

This disclosure generally relates to scheduling systems for notifying physicians of potential patient appointments that have been matched to the physician via a search engine.

BACKGROUND

Users seeking medical care or treatment may wish to select a particular physician or healthcare provider to visit to receive the care or treatment. Factors that may be considered when trying to select a particular provider may include costs, location, specialty, the provider's experience, etc. Currently, information about healthcare providers is available via user-generated reviews on review websites. A user seeking a particular type of healthcare provider or a specific medical treatment may be able to search the review websites for physicians in the particular type or performing the specific treatment. However, user-generated reviews are highly subjective, and may have incomplete information about a particular provider, or incomplete information about the available providers within a given geographic area. Additionally, user-generated reviews may be submitted by other users whose characteristics or demographic information differ from those of the seeking user, making these reviews less applicable to the seeking user.

DESCRIPTION OF EXAMPLE EMBODIMENTS

System Overview

Figure 1:
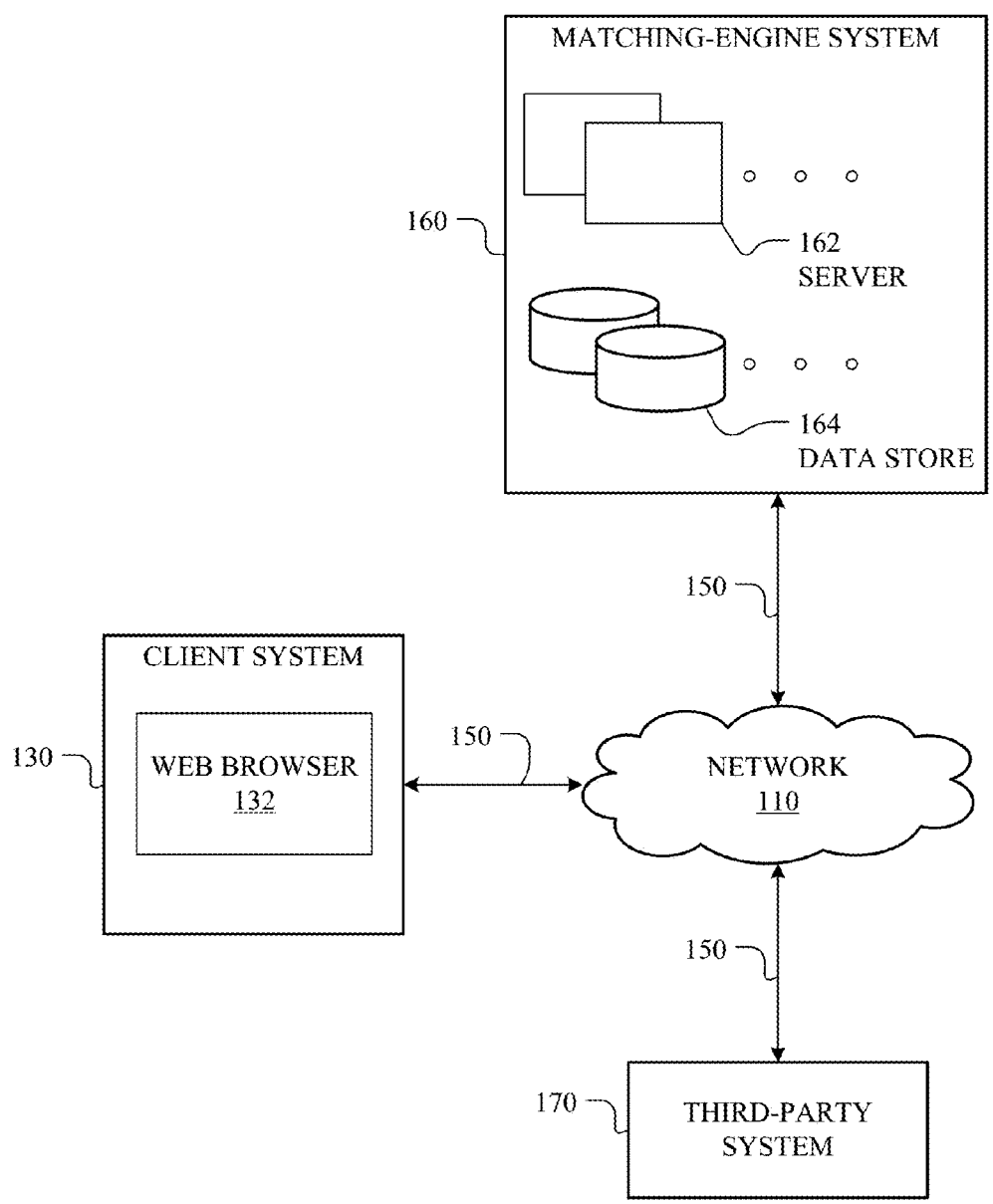
FIG. 1 illustrates an example network environment associated with a matching-engine system.

FIG. 1 illustrates an example network environment 100 associated with a matching-engine system. Network environment 100 includes a client system 130, a matching-engine system 160, and a third-party system 170 connected to each other by a network 110. Although FIG. 1 illustrates a particular arrangement of client system 130, matching-engine system 160, third-party system 170, and network 110, this disclosure contemplates any suitable arrangement of client system 130, matching-engine system 160, third-party system 170, and network 110. As an example and not by way of limitation, two or more of client system 130, matching-engine system 160, and third-party system 170 may be connected to each other directly, bypassing network 110. As another example, two or more of client system 130, matching-engine system 160, and third-party system 170 may be physically or logically co-located with each other in whole or in part. Moreover, although FIG. 1 illustrates a particular number of client systems 130, matching-engine systems 160, third-party systems 170, and networks 110, this disclosure contemplates any suitable number of client systems 130, matching-engine systems 160, third-party systems 170, and networks 110. As an example and not by way of limitation, network environment 100 may include multiple client system 130, matching-engine systems 160, third-party systems 170, and networks 110.

This disclosure contemplates any suitable network 110. As an example and not by way of limitation, one or more portions of network 110 may include an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, or a combination of two or more of these. Network 110 may include one or more networks 110.

Links 150 may connect client system 130, matching-engine system 160, and third-party system 170 to communication network 110 or to each other. This disclosure contemplates any suitable links 150. In particular embodiments, one or more links 150 include one or more wireline (such as for example Digital Subscriber Line (DSL) or Data Over Cable Service Interface Specification (DOCSIS)), wireless (such as for example Wi-Fi or Worldwide Interoperability for Microwave Access (WiMAX)), or optical (such as for example Synchronous Optical Network (SONET) or Synchronous Digital Hierarchy (SDH)) links. In particular embodiments, one or more links 150 each include an ad hoc network, an intranet, an extranet, a VPN, a LAN, a WLAN, a WAN, a WWAN, a MAN, a portion of the Internet, a portion of the PSTN, a cellular technology-based network, a satellite communications technology-based network, another link 150, or a combination of two or more such links 150. Links 150 need not necessarily be the same throughout network environment 100. One or more first links 150 may differ in one or more respects from one or more second links 150.

In particular embodiments, client system 130 may be an electronic device including hardware, software, or embedded logic components or a combination of two or more such components and capable of carrying out the appropriate functionalities implemented or supported by client system 130. As an example and not by way of limitation, a client system 130 may include a computer system such as a desktop computer, notebook or laptop computer, netbook, a tablet computer, e-book reader, GPS device, camera, personal digital assistant (PDA), handheld electronic device, cellular telephone, smartphone, other suitable electronic device, or any suitable combination thereof. This disclosure contemplates any suitable client systems 130. A client system 130 may enable a network user at client system 130 to access network 110. A client system 130 may enable its user to communicate with other users at other client systems 130.

In particular embodiments, client system 130 may include a web browser 132, such as MICROSOFT INTERNET EXPLORER, GOOGLE CHROME or MOZILLA FIREFOX, and may have one or more add-ons, plug-ins, or other extensions, such as TOOLBAR or YAHOO TOOLBAR. A user at client system 130 may enter a Uniform Resource Locator (URL) or other address directing the web browser 132 to a particular server (such as server 162, or a server associated with a third-party system 170), and the web browser 132 may generate a Hyper Text Transfer Protocol (HTTP) request and communicate the HTTP request to server. The server may accept the HTTP request and communicate to client system 130 one or more Hyper Text Markup Language (HTML) files responsive to the HTTP request. Client system 130 may render a webpage based on the HTML files from the server for presentation to the user. This disclosure contemplates any suitable webpage files. As an example and not by way of limitation, webpages may render from HTML files, Extensible Hyper Text Markup Language (XHTML) files, or Extensible Markup Language (XML) files, according to particular needs. Such pages may also execute scripts such as, for example and without limitation, those written in JAVASCRIPT, JAVA, MICROSOFT SILVERLIGHT, combinations of markup language and scripts such as AJAX (Asynchronous JAVASCRIPT and XML), and the like. Herein, reference to a webpage encompasses one or more corresponding webpage files (which a browser may use to render the webpage) and vice versa, where appropriate.

In particular embodiments, matching-engine system 160 may be a network-addressable computing system that can host an online healthcare provider search engine. Matching-engine system 160 may generate, store, receive, and send patient data, healthcare provider data, medical insurance data, or other suitable data related to the healthcare provider search engine. Matching-engine system 160 may identify and rank healthcare providers in general, or according to one or more specified criteria, based on a verity of information. Matching-engine system 160 may be accessed by the other components of network environment 100 either directly or via network 110. In particular embodiments, matching-engine system 160 may receive inputs from one or more of a cost engine or a quality engine (which may be independent systems or sub-systems of matching-engine system 160). The cost engine may receive data about healthcare provider costs (e.g., from the healthcare providers directly, insurance companies, governmental agencies, patients, etc.) and calculate an estimated cost for various medical procedures. The quality engine may receive data about healthcare provider quality (e.g., from public records, surveys, healthcare providers, rating sites, insurance companies, governmental agencies, patients, etc.) and calculate an estimated quality of the healthcare provider in general, or according to one or more specified criteria. In particular embodiments, matching-engine system 160 may include one or more servers 162. Each server 162 may be a unitary server or a distributed server spanning multiple computers or multiple datacenters. Servers 162 may be of various types, such as, for example and without limitation, web server, news server, mail server, message server, advertising server, file server, application server, exchange server, database server, proxy server, another server suitable for performing functions or processes described herein, or any combination thereof. In particular embodiments, each server 162 may include hardware, software, or embedded logic components or a combination of two or more such components for carrying out the appropriate functionalities implemented or supported by server 162. In particular embodiments, matching-engine system 164 may include one or more data stores 164. Data stores 164 may be used to store various types of information. In particular embodiments, the information stored in data stores 164 may be organized according to specific data structures. In particular embodiments, each data store 164 may be a relational, columnar, correlation, or other suitable database. Although this disclosure describes or illustrates particular types of databases, this disclosure contemplates any suitable types of databases. Particular embodiments may provide interfaces that enable a client system 130, a matching-engine system 160, or a third-party system 170 to manage, retrieve, modify, add, or delete, the information stored in data store 164.

In particular embodiments, matching-engine system 160 may be capable of linking a variety of entities. As an example and not by way of limitation, matching-engine system 160 may enable users to interact with each other as well as receive content from third-party systems 170 or other entities, or to allow users to interact with these entities through an application programming interfaces (API) or other communication channels.

In particular embodiments, a third-party system 170 may include one or more types of servers, one or more data stores, one or more interfaces, including but not limited to APIs, one or more web services, one or more content sources, one or more networks, or any other suitable components, e.g., that servers may communicate with. A third-party system 170 may be operated by a different entity from an entity operating matching-engine system 160. In particular embodiments, however, matching-engine system 160 and third-party systems 170 may operate in conjunction with each other to provide search engine services to users of matching-engine system 160 or third-party systems 170. In this sense, matching-engine system 160 may provide a platform, or backbone, which other systems, such as third-party systems 170, may use to provide search engine services and functionality to users across the Internet.

In particular embodiments, matching-engine system 160 also includes user-generated content objects, which may enhance a user's interactions with matching-engine system 160. User-generated content may include anything a user can add, upload, send, or "post" to matching-engine system 160. As an example and not by way of limitation, a user communicates posts to matching-engine system 160 from a client system 130. Posts may include data such as health records, other textual data, location information, photos, videos, links, or other similar data or content. Content may also be added to matching-engine system 160 by a third-party (for example, from healthcare providers, insurance companies, etc.) through a suitable communication channel.

In particular embodiments, matching-engine system 160 may include a variety of servers, sub-systems, programs, modules, logs, and data stores. In particular embodiments, matching-engine system 160 may include one or more of the following: a web server, action logger, API-request server, relevance-and-ranking engine, content-object classifier, notification controller, action log, third-party-content-object-exposure log, inference module, authorization/privacy server, search module, advertisement-targeting module, user-interface module, user/patient-profile store, connection store, third-party content store, or location store. Matching-engine system 160 may also include suitable components such as network interfaces, security mechanisms, load balancers, failover servers, management-and-network-operations consoles, other suitable components, or any suitable combination thereof. In particular embodiments, matching-engine system 160 may include one or more user-profile stores for storing user profiles. A user/patient profile may include, for example, medical information, biographic information, demographic information, behavioral information, social information, or other types of descriptive information, such as work experience, educational history, hobbies or preferences, interests, affinities, or location. A web server may be used for linking matching-engine system 160 to one or more client systems 130 or one or more third-party system 170 via network 110. The web server may include a mail server or other messaging functionality for receiving and routing messages between matching-engine system 160 and one or more client systems 130. An API-request server may allow a third-party system 170 to access information from matching-engine system 160 by calling one or more APIs. An action logger may be used to receive communications from a web server about a user's actions on or off matching-engine system 160. In conjunction with the action log, a third-party-content-object log may be maintained of user exposures to third-party-content objects. A notification controller may provide information regarding content objects to a client system 130. Information may be pushed to a client system 130 as notifications, or information may be pulled from client system 130 responsive to a request received from client system 130. Authorization servers may be used to enforce one or more privacy settings of the users of matching-engine system 160. A privacy setting of a user determines how particular information associated with a user can be shared. The authorization server may allow users to opt in to or opt out of having their actions logged by matching-engine system 160 or shared with other systems (e.g., third-party system 170), such as, for example, by setting appropriate privacy settings. Third-party-content-object stores may be used to store content objects received from third parties, such as a third-party system 170. Location stores may be used for storing location information received from client systems 130 associated with users.

Systems and Methods

Figure 2:
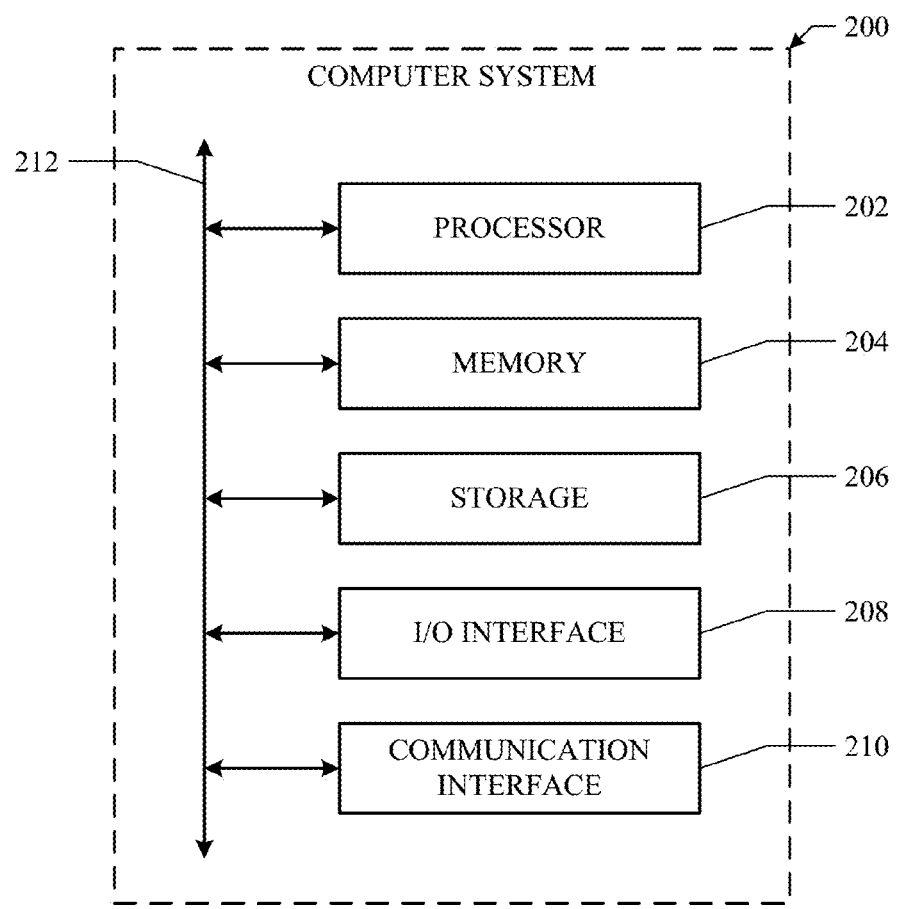
FIG. 2 illustrates an example computer system.

FIG. 2 illustrates an example computer system 200. In particular embodiments, one or more computer systems 200 perform one or more steps of one or more methods described or illustrated herein. In particular embodiments, one or more computer systems 200 provide functionality described or illustrated herein. In particular embodiments, software running on one or more computer systems 200 performs one or more steps of one or more methods described or illustrated herein or provides functionality described or illustrated herein. Particular embodiments include one or more portions of one or more computer systems 200. Herein, reference to a computer system may encompass a computing device, and vice versa, where appropriate. Moreover, reference to a computer system may encompass one or more computer systems, where appropriate.

This disclosure contemplates any suitable number of computer systems 200. This disclosure contemplates computer system 200 taking any suitable physical form. As example and not by way of limitation, computer system 200 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, or a combination of two or more of these. Where appropriate, computer system 200 may include one or more computer systems 200; be unitary or distributed; span multiple locations; span multiple machines; span multiple data centers; or reside in a cloud, which may include one or more cloud components in one or more networks. Where appropriate, one or more computer systems 200 may perform without substantial spatial or temporal limitation one or more steps of one or more methods described or illustrated herein. As an example and not by way of limitation, one or more computer systems 200 may perform in real time or in batch mode one or more steps of one or more methods described or illustrated herein. One or more computer systems 200 may perform at different times or at different locations one or more steps of one or more methods described or illustrated herein, where appropriate.

In particular embodiments, computer system 200 includes a processor 202, memory 204, storage 206, an input/output (I/O) interface 208, a communication interface 210, and a bus 212. Although this disclosure describes and illustrates a particular computer system having a particular number of particular components in a particular arrangement, this disclosure contemplates any suitable computer system having any suitable number of any suitable components in any suitable arrangement.

In particular embodiments, processor 202 includes hardware for executing instructions, such as those making up a computer program. As an example and not by way of limitation, to execute instructions, processor 202 may retrieve (or fetch) the instructions from an internal register, an internal cache, memory 204, or storage 206; decode and execute them; and then write one or more results to an internal register, an internal cache, memory 204, or storage 206. In particular embodiments, processor 202 may include one or more internal caches for data, instructions, or addresses. This disclosure contemplates processor 202 including any suitable number of any suitable internal caches, where appropriate. As an example and not by way of limitation, processor 202 may include one or more instruction caches, one or more data caches, and one or more translation lookaside buffers (TLBs). Instructions in the instruction caches may be copies of instructions in memory 204 or storage 206, and the instruction caches may speed up retrieval of those instructions by processor 202. Data in the data caches may be copies of data in memory 204 or storage 206 for instructions executing at processor 202 to operate on; the results of previous instructions executed at processor 202 for access by subsequent instructions executing at processor 202 or for writing to memory 204 or storage 206; or other suitable data. The data caches may speed up read or write operations by processor 202. The TLBs may speed up virtual-address translation for processor 202. In particular embodiments, processor 202 may include one or more internal registers for data, instructions, or addresses. This disclosure contemplates processor 202 including any suitable number of any suitable internal registers, where appropriate. Where appropriate, processor 202 may include one or more arithmetic logic units (ALUs); be a multi-core processor; or include one or more processors 202. Although this disclosure describes and illustrates a particular processor, this disclosure contemplates any suitable processor.

In particular embodiments, memory 204 includes main memory for storing instructions for processor 202 to execute or data for processor 202 to operate on. As an example and not by way of limitation, computer system 200 may load instructions from storage 206 or another source (such as, for example, another computer system 200) to memory 204. Processor 202 may then load the instructions from memory 204 to an internal register or internal cache. To execute the instructions, processor 202 may retrieve the instructions from the internal register or internal cache and decode them. During or after execution of the instructions, processor 202 may write one or more results (which may be intermediate or final results) to the internal register or internal cache. Processor 202 may then write one or more of those results to memory 204. In particular embodiments, processor 202 executes only instructions in one or more internal registers or internal caches or in memory 204 (as opposed to storage 206 or elsewhere) and operates only on data in one or more internal registers or internal caches or in memory 204 (as opposed to storage 206 or elsewhere). One or more memory buses (which may each include an address bus and a data bus) may couple processor 202 to memory 204. Bus 212 may include one or more memory buses, as described below. In particular embodiments, one or more memory management units (MMUs) reside between processor 202 and memory 204 and facilitate accesses to memory 204 requested by processor 202. In particular embodiments, memory 204 includes random access memory (RAM). This RAM may be volatile memory, where appropriate. Where appropriate, this RAM may be dynamic RAM (DRAM) or static RAM (SRAM). Moreover, where appropriate, this RAM may be single-ported or multi-ported RAM. This disclosure contemplates any suitable RAM. Memory 204 may include one or more memories 204, where appropriate. Although this disclosure describes and illustrates particular memory, this disclosure contemplates any suitable memory.

In particular embodiments, storage 206 includes mass storage for data or instructions. As an example and not by way of limitation, storage 206 may include a hard disk drive (HDD), a floppy disk drive, flash memory, an optical disc, a magneto-optical disc, magnetic tape, or a Universal Serial Bus (USB) drive or a combination of two or more of these. Storage 206 may include removable or non-removable (or fixed) media, where appropriate. Storage 206 may be internal or external to computer system 200, where appropriate. In particular embodiments, storage 206 is non-volatile, solid-state memory. In particular embodiments, storage 206 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 206 taking any suitable physical form. Storage 206 may include one or more storage control units facilitating communication between processor 202 and storage 206, where appropriate. Where appropriate, storage 206 may include one or more storages 206. Although this disclosure describes and illustrates particular storage, this disclosure contemplates any suitable storage.

In particular embodiments, I/O interface 208 includes hardware, software, or both, providing one or more interfaces for communication between computer system 200 and one or more I/O devices. Computer system 200 may include one or more of these I/O devices, where appropriate. One or more of these I/O devices may enable communication between a person and computer system 200. As an example and not by way of limitation, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 208 for them. Where appropriate, I/O interface 208 may include one or more device or software drivers enabling processor 202 to drive one or more of these I/O devices. I/O interface 208 may include one or more I/O interfaces 208, where appropriate. Although this disclosure describes and illustrates a particular I/O interface, this disclosure contemplates any suitable I/O interface.

In particular embodiments, communication interface 210 includes hardware, software, or both providing one or more interfaces for communication (such as, for example, packet-based communication) between computer system 200 and one or more other computer systems 200 or one or more networks. As an example and not by way of limitation, communication interface 210 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 210 for it. As an example and not by way of limitation, computer system 200 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 200 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 200 may include any suitable communication interface 210 for any of these networks, where appropriate. Communication interface 210 may include one or more communication interfaces 210, where appropriate. Although this disclosure describes and illustrates a particular communication interface, this disclosure contemplates any suitable communication interface.

In particular embodiments, bus 212 includes hardware, software, or both coupling components of computer system 200 to each other. As an example and not by way of limitation, bus 212 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 212 may include one or more buses 212, where appropriate. Although this disclosure describes and illustrates a particular bus, this disclosure contemplates any suitable bus or interconnect.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

This disclosure contemplates one or more computer-readable storage media implementing any suitable storage. In particular embodiments, a computer-readable storage medium implements one or more portions of processor 202 (such as, for example, one or more internal registers or caches), one or more portions of memory 204, one or more portions of storage 206, or a combination of these, where appropriate. In particular embodiments, a computer-readable storage medium implements RAM or ROM. In particular embodiments, a computer-readable storage medium implements volatile or persistent memory. In particular embodiments, one or more computer-readable storage media embody software. Herein, reference to software may encompass one or more applications, bytecode, one or more computer programs, one or more executables, one or more instructions, logic, machine code, one or more scripts, or source code, and vice versa, where appropriate. In particular embodiments, software includes one or more application programming interfaces (APIs). This disclosure contemplates any suitable software written or otherwise expressed in any suitable programming language or combination of programming languages. In particular embodiments, software is expressed as source code or object code. In particular embodiments, software is expressed in a higher-level programming language, such as, for example, C, Perl, or a suitable extension thereof. In particular embodiments, software is expressed in a lower-level programming language, such as assembly language (or machine code). In particular embodiments, software is expressed in JAVA. In particular embodiments, software is expressed in Hyper Text Markup Language (HTML), Extensible Markup Language (XML), or other suitable markup language.

Figure 3:
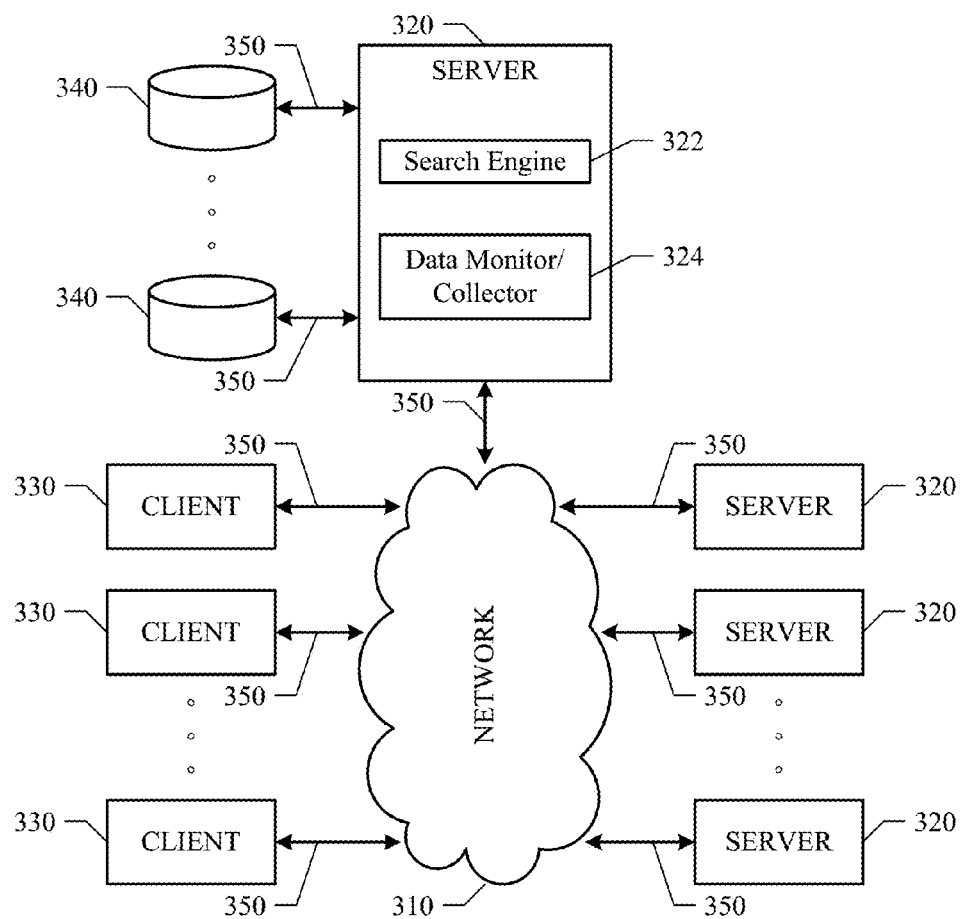
FIG. 3 illustrates an example network environment.

FIG. 3 illustrates an example network environment 300. This disclosure contemplates any suitable network environment 300. As an example and not by way of limitation, although this disclosure describes and illustrates a network environment 300 that implements a client-server model, this disclosure contemplates one or more portions of a network environment 300 being peer-to-peer, where appropriate. Particular embodiments may operate in whole or in part in one or more network environments 300. In particular embodiments, one or more elements of network environment 300 provide functionality described or illustrated herein. Particular embodiments include one or more portions of network environment 300. Network environment 300 includes a network 310 coupling one or more servers 320 and one or more clients 330 to each other. This disclosure contemplates any suitable network 310. As an example and not by way of limitation, one or more portions of network 310 may include an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, or a combination of two or more of these. Network 310 may include one or more networks 310.

Links 350 couple servers 320 and clients 330 to network 310 or to each other. This disclosure contemplates any suitable links 350. As an example and not by way of limitation, one or more links 350 each include one or more wireline (such as, for example, Digital Subscriber Line (DSL) or Data Over Cable Service Interface Specification (DOCSIS)), wireless (such as, for example, Wi-Fi or Worldwide Interoperability for Microwave Access (WiMAX)) or optical (such as, for example, Synchronous Optical Network (SONET) or Synchronous Digital Hierarchy (SDH)) links 350. In particular embodiments, one or more links 350 each includes an intranet, an extranet, a VPN, a LAN, a WLAN, a WAN, a MAN, a communications network, a satellite network, a portion of the Internet, or another link 350 or a combination of two or more such links 350. Links 350 need not necessarily be the same throughout network environment 300. One or more first links 350 may differ in one or more respects from one or more second links 350.

This disclosure contemplates any suitable servers 320. As an example and not by way of limitation, one or more servers 320 may each include one or more advertising servers, applications servers, catalog servers, communications servers, database servers, exchange servers, fax servers, file servers, game servers, home servers, mail servers, message servers, news servers, name or DNS servers, print servers, proxy servers, sound servers, standalone servers, web servers, or web-feed servers. In particular embodiments, a server 320 includes hardware, software, or both for providing the functionality of server 320. As an example and not by way of limitation, a server 320 that operates as a web server may be capable of hosting websites containing web pages or elements of web pages and include appropriate hardware, software, or both for doing so. In particular embodiments, a web server may host HTML or other suitable files or dynamically create or constitute files for web pages on request. In response to a Hyper Text Transfer Protocol (HTTP) or other request from a client 330, the web server may communicate one or more such files to client 330. As another example, a server 320 that operates as a mail server may be capable of providing e-mail services to one or more clients 330. As another example, a server 320 that operates as a database server may be capable of providing an interface for interacting with one or more data stores (such as, for example, data stores 340 described below). Where appropriate, a server 320 may include one or more servers 320; be unitary or distributed; span multiple locations; span multiple machines; span multiple datacenters; or reside in a cloud, which may include one or more cloud components in one or more networks.

In particular embodiments, one or more links 350 may couple a server 320 to one or more data stores 340. A data store 340 may store any suitable information, and the contents of a data store 340 may be organized in any suitable manner. As an example and not by way or limitation, the contents of a data store 340 may be stored as a dimensional, flat, hierarchical, network, object-oriented, relational, XML, or other suitable database or a combination or two or more of these. A data store 340 (or a server 320 coupled to it) may include a database-management system or other hardware or software for managing the contents of data store 340. The database-management system may perform read and write operations, delete or erase data, perform data deduplication, query or search the contents of data store 340, or provide other access to data store 340.

In particular embodiments, one or more servers 320 may each include one or more search engines 322. A search engine 322 may include hardware, software, or both for providing the functionality of search engine 322. As an example and not by way of limitation, a search engine 322 may implement one or more search algorithms to identify network resources in response to search queries received at search engine 322, one or more ranking algorithms to rank identified network resources, or one or more summarization algorithms to summarize identified network resources. In particular embodiments, a ranking algorithm implemented by a search engine 322 may use a machine-learned ranking formula, which the ranking algorithm may obtain automatically from a set of training data constructed from pairs of search queries and selected Uniform Resource Locators (URLs), where appropriate.

In particular embodiments, one or more servers 320 may each include one or more data monitors/collectors 324. A data monitor/collection 324 may include hardware, software, or both for providing the functionality of data collector/collector 324. As an example and not by way of limitation, a data monitor/collector 324 at a server 320 may monitor and collect network-traffic data at server 320 and store the network-traffic data in one or more data stores 340. In particular embodiments, server 320 or another device may extract pairs of search queries and selected URLs from the network-traffic data, where appropriate.

This disclosure contemplates any suitable clients 330. A client 330 may enable a user at client 330 to access or otherwise communicate with network 310, servers 320, or other clients 330. As an example and not by way of limitation, a client 330 may have a web browser, such as MICROSOFT INTERNET EXPLORER or MOZILLA FIREFOX, and may have one or more add-ons, plug-ins, or other extensions, such as GOOGLE TOOLBAR or YAHOO TOOLBAR. A client 330 may be an electronic device including hardware, software, or both for providing the functionality of client 330. As an example and not by way of limitation, a client 330 may, where appropriate, be an embedded computer system, an SOC, an SBC (such as, for example, a COM or SOM), a desktop computer system, a laptop or notebook computer system, an interactive kiosk, a mainframe, a mesh of computer systems, a mobile telephone, a PDA, a netbook computer system, a server, a tablet computer system, or a combination of two or more of these. Where appropriate, a client 330 may include one or more clients 330; be unitary or distributed; span multiple locations; span multiple machines; span multiple datacenters; or reside in a cloud, which may include one or more cloud components in one or more networks.

Matching Engine

In particular embodiments, a user of matching-engine system 160 may send a query to matching-engine system 160 for a recommendation of one or more physicians. The query may comprise a specific medical condition, one or more symptoms, one or more names of a medical specialty, or a type of medical procedure. As an example and not by way of limitation, a user may send a query regarding physicians to treat plantar fasciitis. As another example, a user may send a query merely stating that the user has a headache and nausea, and request one or more physicians to help with the user's symptoms. As another example, a user may send a query for physicians able to perform a colonoscopy. In particular embodiments, a user may send separate queries for one or more symptoms, conditions, or treatments. In particular embodiments, a user may send a single query containing several distinct symptoms, conditions, or treatments. As an example and not by way of limitation, a user may submit a query that comprises an indication that the user needs an annual physical, and also that the user has stomach pains. Matching-engine system 160 may provide the user with a set of recommended physicians for an annual physical, and a second set of recommended physicians for the stomach pain. In particular embodiments, matching-engine system 160 may send the user a single set of recommended physicians, wherein the set comprises recommended physicians for the annual physical and recommended physicians for the stomach pain. In particular embodiments, there may be an overlap between the two different sets of recommended physicians.

In particular embodiments, matching-engine system 160 may recommend one or more physicians for a user to visit within a particular geographic region in which the user resides or works. In particular embodiments, the geographic region may be a metropolitan statistical area, or MSA. MSAs are defined metropolitan regions determined by the United States Office of Management and Budget. As an example and not by way of limitation, matching-engine system 160 may recommend physicians who are located within the Los Angeles-Long Beach-Anaheim MSA. In particular embodiments, matching-engine system 160 may recommend one or more physicians who are within a preset distance of the location of the user. As an example and not by way of limitation, matching-engine system 160 may only recommend physicians who are within 25 miles of the user. In particular embodiments, the user may specify a distance or region in which to look for physicians to recommend. As an example and not by way of limitation, a user may indicate that she only wants to view recommended physicians within Orange County, Calif., without receiving recommendations for physicians within Los Angeles, Calif.

In particular embodiments, parameters for recommending one or more physicians to a user may be provided by an administrator of the particular user's health plan. As an example and not by way of limitation, if a user receives her health insurance coverage through her employment, and her employer has an administrator responsible for determining the health-care coverage to be provided by the employer, then the administrator may specify an acceptable range of parameters within which to recommend physicians. For example, the administrator may wish to specify a range of acceptable performance scores for physicians, acceptable monetary costs for physicians when conducting particular treatments or procedures, or an acceptable range of experience indices for physicians. In particular embodiments, performance score may represent a physician's efficiency in time and resources in treating a patient for a particular condition or disease, or in applying a particular treatment method. A performance score may be of interest to both a patient and the patient's insurance provider as an indication that a physician will require less time, office visits, resources, etc. In particular embodiments, an experience index for a physician may indicate the physician's experience in dealing with a particular condition or disease, or in performing a particular treatment method. In particular embodiments, the experience index may also represent how many different types of conditions within a condition group a physician has seen. These parameters may allow the administrator to direct users towards physicians that the administrator has determined are cost-effective physicians, or in the alternative, physicians that are above a threshold baseline of competency while remaining affordable for the employer. In particular embodiments, when a user of the health-care plan run by that administrator submits a query for one or more physicians, matching-engine system 160 may only present physicians meeting the acceptable parameters specified by the administrator. In particular embodiments, matching-engine system 160 may include other physicians, but may rank the physicians meeting the administrator's parameters more highly.

Figure 4:
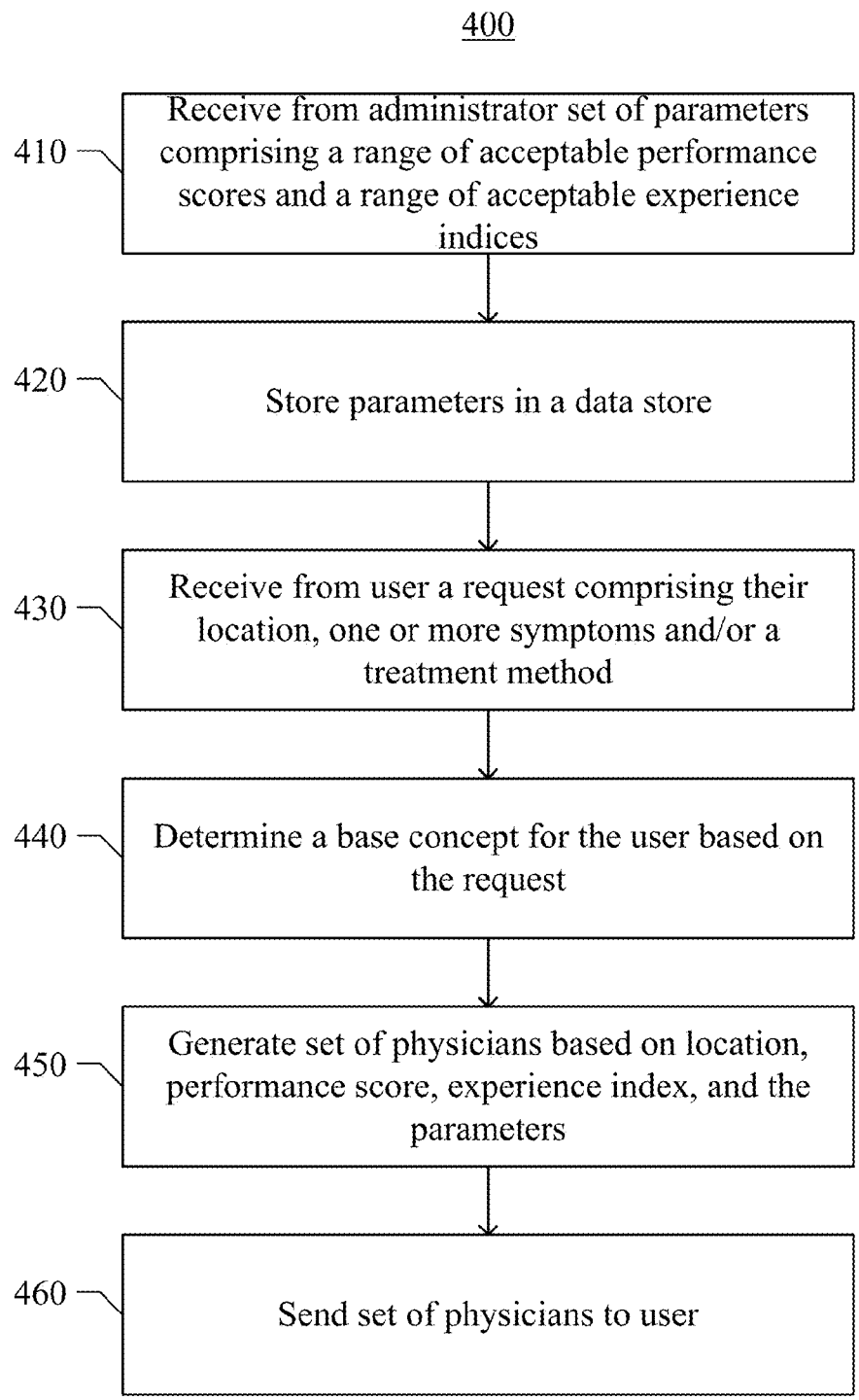
FIG. 4 illustrates an example method of using a matching-engine system.

FIG. 4 illustrates an example method for using matching-engine system 160 to provide one or more recommended physicians to a particular user. At step 410, matching-engine system 160 may receive from an administrator a set of parameters. In particular embodiments, the set of parameters may comprise a range of acceptable performance scores, a range of acceptable experience indices, or a range of acceptable costs. At step 420, matching-engine system 160 may store the set of parameters in a database, associating the set of parameters with a group of one or more users corresponding to the administrator. As an example and not by way of limitation, the group of users may comprise the employees on an employer-provided health-care plan. At step 430, matching-engine system 160 may receive from one of the group of users a request, wherein the request comprises at least the user's geographic location, and one or more symptoms or a treatment method. As an example and not by way of limitation, user Alice may send a request which includes information indicating that she resides in Mountain View, Calif., and she has stomach pains and nausea. As another example, user Zeke may send a request which includes information indicating that his location is Evanston, Ill., and he is seeking a physician for rotator cuff surgery. At step 440, matching-engine system 160 may determine at least one base concept associated with the user's request. As an example and not by way of limitation, in the examples given above, matching-engine system 160 may determine a base concept of "rotator cuff surgery" for Zeke, and a base concept of "stomach ache" for Alice. At step 450, matching-engine system 160 may generate a set of one or more physicians to recommend to the user for the determined base concept. Matching-engine system 160 may also consider the location of the user and locations of the physicians, and the performance scores and experience indices for each physician relevant to the base concept, and whether they are within the parameters defined by the administrator. At step 460, matching-engine system 160 may send the set of recommended physicians to the user.

Particular embodiments may repeat one or more steps of the method of FIG. 4, where appropriate. Although this disclosure describes and illustrates particular steps of the method of FIG. 4 as occurring in a particular order, this disclosure contemplates any suitable steps of the method of FIG. 4 occurring in any suitable order. Moreover, although this disclosure describes and illustrates particular components, devices, or systems carrying out particular steps of the method of FIG. 4, this disclosure contemplates any suitable combination of any suitable components, devices, or systems carrying out any suitable steps of the method of FIG. 4.

In particular embodiments, matching-engine system 160 may receive as an input one or more performance scores associated with particular physicians in generating a set of recommended physicians. Matching-engine system 160 may receive from a physician or health-care provider one or more Current Procedural Terminology (CPT) codes, each of which corresponds to a medical, surgical, or diagnostic service. As an example and not by way of limitation, matching-engine system 160 may receive a CPT code for patient Alice after a visit to Dr. Bob, which may indicate that patient Alice received a standard blood panel test. Matching-engine system 160 may also receive one or more International Classification of Diseases (ICD) codes, each of which corresponds to a particular disease or condition. In particular embodiments, an insurance provider may not pay for medical services provided to a particular insured patient unless the CPT codes for the services provided correlate with the ICD codes assigned to that particular patient visit. As an example and not by way of limitation, an insurance provider may reject for payment the charges for a CPT code indicating a colonoscopy, if the only ICD code assigned to the patient visit indicates that the visit was for a sore throat.

In particular embodiments, the costs incurred by a physician in treating a patient may be considered in monetary cost. In particular embodiments, another metric may be used to calculate costs incurred for treatment which accounts for monetary costs as well as labor costs and overall resources involved for the treatment. As an example and not by way of limitation, matching-engine system 160 may consider the costs in terms of resource value units, or RVUs. As an example and not by way of limitation, matching-engine system 160 may use RVUs as used by the United States Medicare reimbursement formula for physician services. An RVU may represent a non-monetary relative measure which is scaled by the geographic region in which the treatment occurred. As an example and not by way of limitation, in monetary costs, the same medical procedure may be more expensive in a high cost-of-living area compared to a low cost-of-living area. By adjusting for the cost-of-living or the average cost of medical services in a given area, the RVU may comprise a location-independent measure of costs. In particular embodiments, an RVU may be assigned to each CPT code for particular treatments. In particular embodiments, RVUs may be assigned in advance, such that matching-engine system 160 may receive a CPT code and automatically add the appropriate RVU to the episode of care.

In particular embodiments, matching-engine system 160 may receive the monetary costs for a particular service or treatment as an additional cost factor to the RVU. In particular embodiments, the cost may be a reported average monetary cost per patient per year for a particular base concept, which may be calculated based on the received cost figures during the previous year. In particular embodiments, the average costs per patient per year may be an expected cost for treating the patient. This expected cost may then be compared against the actual costs incurred by a physician in treating the patient, by converting the RVUs incurred in treatment back into monetary costs. As an example and not by way of limitation, the average cost per year for treating a particular disease may be expected to be $7,500. If a physician treating the disease may incur costs of 120 RVUs, and the conversion rate for an RVU in this particular specialty is estimated at $55.00/RVU, then the actual costs incurred by this physician in treating the disease may be 120*$55.00, or $6,600. Comparing the RVU costs to the estimated costs may show that this physician is $900 more efficient in treating this particular disease than expected.

In particular embodiments, matching-engine system 160 may include other factors in calculating a performance score, such as administrative costs or non-physician services costs. As an example and not by way of limitation, if a first treatment method requires five office visits, and a second treatment method requires two office visits, matching-engine system 160 may determine that the first treatment method will have higher additional costs in terms of time required by the patient, and administrative costs in processing additional office visits.

In particular embodiments, a performance score for a physician may reflect an indication of the amount of health-care resources used by the physician or health-care provider in delivery of care for treating patients with the same or similar clinical complexity. Complex treatments may result in more resources being consumed than simple cases regardless of physician skills, but there may be a variation in how much resources are used. The performance score may identify physicians who are using relatively less resources than the peer group, and by how much. Determination of the performance score is discussed in further detail below.

In particular embodiments, matching-engine system 160 may also receive and use as an input one or more experience indices associated with a particular physician. The experience index for a physician may be an indication of how much experience a physician has in a particular specialty or with a particular disease or condition, based on the number of patients seen with the particular specialty or disease or condition, and the severity of each patient seen. In particular embodiments, matching-engine system 160 may consider the case volume seen by a particular physician within a particular specialty, which may represent a proportional volume of cases for a particular disease seen by the particular physician versus all other physicians in the same specialty. As an example and not by way of limitation, if there were 100 separate patient visits for diagnosis or treatment of non-Hodgkins lymphoma in the Chicago metropolitan area in 2013, and 25 of those visits were to Dr. Moore, matching-engine system 160 may consider Dr. Moore's case volume for non-Hodgkins lymphoma to be 0.25, or 25 divided by the 100 total cases. In particular embodiments, the experience index may also represent a variety of diseases seen by a particular physician within a particular specialty. In particular embodiments, the experience index may consider three factors: volume, variety, and severity. The severity may be measured by a Boolean scale: chronic, or non-chronic, using the Chronic Conditions Indication database from the Healthcare Cost Institute. Determination of the experience index is discussed in detail further below.

Performance Engine

In particular embodiments, a performance engine of matching-engine system 160 may determine one or more performance scores for a particular physician based on data received about episodes of care associated with the particular physician. An episode of care may represent all interactions between a patient and a physician for a particular disease or treatment. In particular embodiments, using an episode of care as the base point for determining performance scores may be more accurate than determining performance merely based on cost. As an example and not by way of limitation, if Dr. Alan has a lower average cost than Dr. Brad for medical services, but Dr. Alan requires more tests and more office visits to treat the same disease as Dr. Brad, the individual service costs may point to Dr. Alan as having better performance (e.g. lower cost for the same services), but the overall episode of care may point to Dr. Brad as having better overall performance in treating the disease, which may be a better indicator of doctor efficiency.

In particular embodiments, an episode of care may comprise a collection of all clinically related procedure and diagnosis codes for treating an index disease or condition for a particular patient from the onset of the index disease or condition to closure. An episode of care may comprise a record of all encounters between a patient and a health-care provider. In particular embodiments, an episode of care may be defined over a single calendar year. As an example and not by way of limitation, if a patient Alice starts visiting a doctor Bob for her Type-2 diabetes on Jul. 1, 2013, and continues to see Dr. Bob for her diabetes with monthly visits through August, 2014, matching-engine system 160 may consider Alice to have two episodes of care with Dr. Bob: one episode of care for diabetes in 2013, and a second episode of care for diabetes in 2014. In particular embodiments, a particular patient may only be associated with a single episode of care at a time. If the patient starts visiting a new doctor, or starts being treated for a new primary condition, a new episode of care may be determined. As an example and not by way of limitation, if Alice has been visiting Dr. Bob for her diabetes through August 2014, but then breaks her leg and starts seeing Dr. Bob for treatment of the broken leg for two months, matching-engine system 160 may determine a new episode of care for Alice and Dr. Bob with a new primary condition of "broken leg" from August 2014 to October 2014. If Alice's leg heals and she continues seeing Dr. Bob for her diabetes, matching-engine system 160 may determine a third episode of care for Alice and Dr. Bob for diabetes. In particular embodiments, matching-engine system 160 may determine a single episode of care for 2014 for Alice and Dr. Bob for a primary condition of diabetes, with a time period of January to August 2014, and October to December 2014.

In particular embodiments, an episode of care may be associated with a single base concept. The base concept may represent the primary disease or condition being treated by the visits comprising the episode of care. In particular embodiments, the base concept may be identified using a clinical taxonomy. A clinical taxonomy may comprise a table of medical terminology with corresponding laymen's terms for the medical term. As an example and not by way of limitation, a patient may visit a doctor for a "broken leg." Matching-engine system 160 may determine record the visit as an episode of care with a base concept of "tibial plateau fracture." In particular embodiments, matching-engine system 160 may additionally record one or more sub-concepts associated with the base concept. Each sub-type may represent an additional diagnoses, conditions or diseases that the patient has which could introduce complications in treatment of the base concept. As an example and not by way of limitation, if a patient who is making a physician visit for a broken leg also has osteoporosis, matching-engine system 160 may record an episode of care as having a base concept of "tibial plateau fracture," with a sub-concept of "osteoporosis." Including the sub-types may ensure that physicians are not evaluated simply based on how they are able to treat the base concept. The simultaneous presence of additional conditions in a patient may likely create additional resource burdens, which may lead to additional treatment costs. As an example and not by way of limitation, if Dr. Bob is treating a patient for a broken leg with no other sub-concepts involved, and Dr. Charles is treating a patient for a broken leg with a sub-concept of osteoporosis, Dr. Charles may require additional resources in treating the base concept condition of the broken leg. However, comparing the two episodes of care without any adjustment for the sub-concept may not accurately represent each physician's performance in treating a broken leg, and may lead to false negatives in evaluation of the physicians.

In particular embodiments, the performance score for a particular physician may be represented as a relational score for the particular physician with respect to similarly-situated physicians. In particular embodiments, similarly-situated physicians may additionally be defined as seeing a similar set of patients which are characterized by attributes of age, gender, place of service, MSA, and disease co-morbidity. In particular embodiments, additional attributes may be used to determine similarly-situated physicians. In particular embodiments, matching-engine system 160 may consider physicians having the same primary specialty. As an example and not by way of limitation, matching-engine system 160 may generate a score that indicates the particular physician's efficiency and performance compared to other physicians that the user may also receive recommendations for. For example, if Drs. Irene, John, and Kyle are the three nephrologists in a particular geographic region, any performance score for Dr. John may represent his relative performance when compared to Drs. Irene and Kyle.

Figure 5:
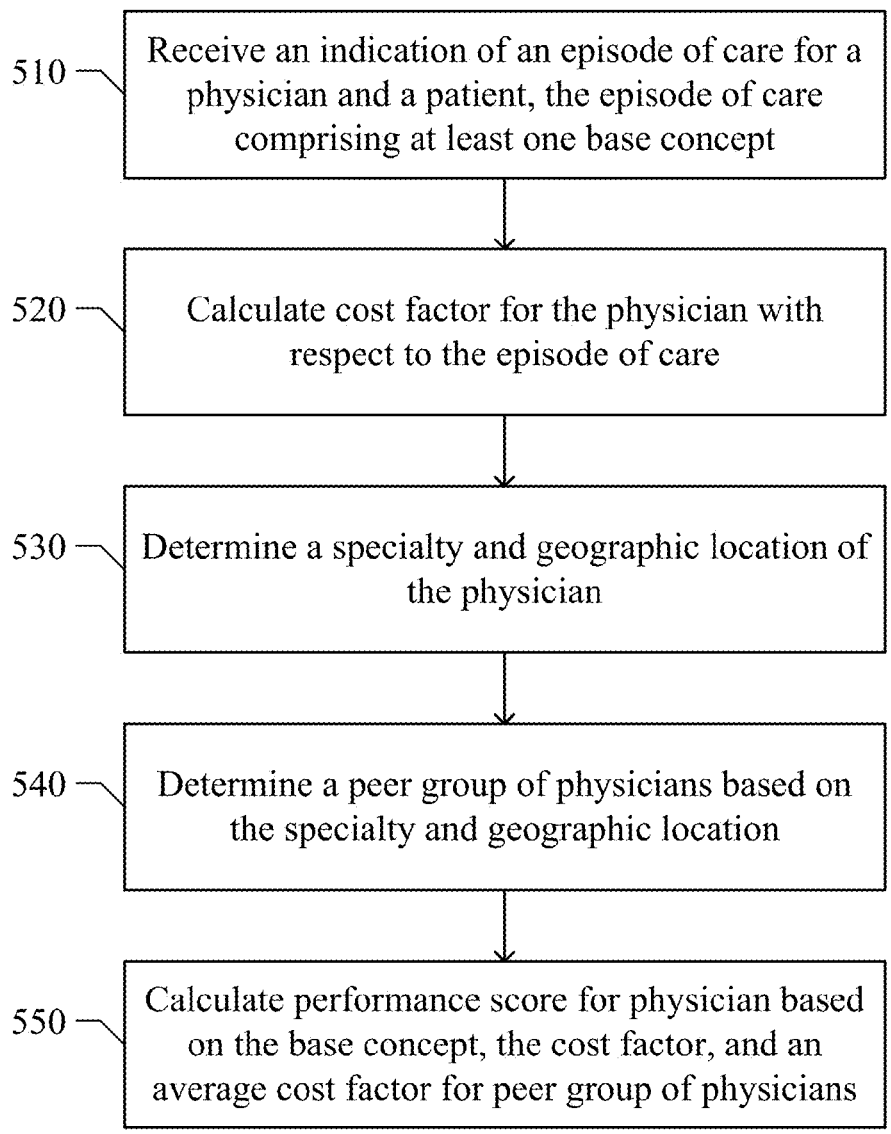
FIG. 5 illustrates an example method of calculating a performance score using a performance engine.

FIG. 5 illustrates an example method for determining a performance score for a physician with respect to a particular episode of care. The method may begin at step 510, where matching-engine system 160 may receive an indication of an episode of care for a particular physician and a particular patient. The indication may comprise a number of diagnosis and treatment codes, such as a set of related CPT codes and ICD codes. Based on the received codes, matching-engine system 160 may determine a base concept for the episode of care. In particular embodiments, matching-engine system 160 may determine one or more sub-concepts that are associated with the base concept of the episode of care. As an example and not by way of limitation, matching-engine system 160 may receive CPT and/or ICD codes within the episode of care that indicate that the patient has at least one secondary condition. At step 520, matching-engine system 160 may calculate a cost factor for the episode of care for the particular physician. In particular embodiments, the cost factor may be the monetary cost of the treatments within the episode of care. In particular embodiments, the cost factor may be a normalized value, such as RVU. In particular embodiments, matching-engine system 160 may consider both the absolute monetary costs expended in treating the episode of care, as well as the RVU. At step 530, matching-engine system 160 may determine at least one specialty of the physician, and a geographic area that the physician practices in. At step 540, the specialty and geographic area of the physician may be used to determine a peer group of one or more other physicians who share a common specialty and practice within the same geographic area as the particular physician. As an example and not by way of limitation, if Dr. Chad is a cardiologist practicing in Denver, Colo., his peer group may be all cardiologists practicing in the Denver area. At step 550, matching-engine system 160 may calculate a performance score for the particular physician with respect to the base concept and the sub-concepts by comparing the cost factor for the episode of care with the cost factors incurred by the peer group of physicians for the same base concept and sub-concepts. As an example and not by way of limitation, if Dr. Chad has an episode of care for a patient with a myocardial infarction and a sub-concept of diabetes, matching-engine system 160 may compare the costs incurred by Dr. Chad for this episode of care with the costs associated with other episodes of care by the other physicians in the peer group with a base concept of myocardial infarction and a sub-concept of diabetes. In particular embodiments, matching-engine system 160 may further determine whether the other physicians in the peer group are seeing patients with similar attributes such as age, gender, place of service, and MSA.

Particular embodiments may repeat one or more steps of the method of FIG. 5, where appropriate. Although this disclosure describes and illustrates particular steps of the method of FIG. 5 as occurring in a particular order, this disclosure contemplates any suitable steps of the method of FIG. 5 occurring in any suitable order. Moreover, although this disclosure describes and illustrates particular components, devices, or systems carrying out particular steps of the method of FIG. 5, this disclosure contemplates any suitable combination of any suitable components, devices, or systems carrying out any suitable steps of the method of FIG. 5.

Figure 6A:
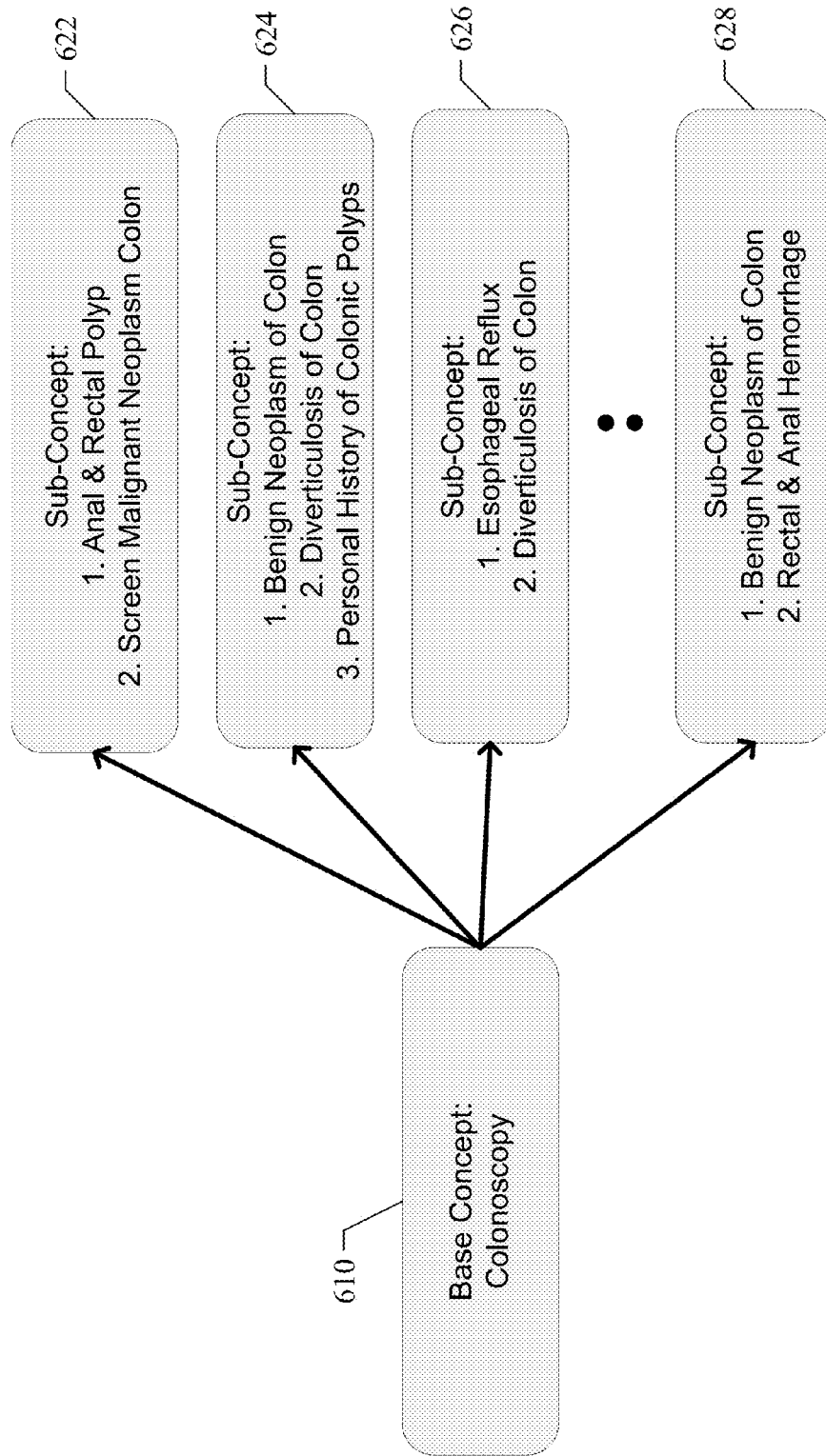
FIG. 6A illustrates an example embodiment of a performance engine comparing a base concept with one or more sub-concept groups.

FIG. 6A illustrates an example embodiment of the performance engine which considers one or more sub-concept groups 622-628 which may be associated with a base concept 610. In particular embodiments, a sub-concept group 622-628 may represent a distinct group of one or more sub-concepts, i.e. secondary conditions. In the example of FIG. 6A, sub-concept groups 624 and 628 share a common sub-concept, but differ in the other sub-concepts. In particular embodiments, several different base concepts 610 may have common sub-concepts 622-628 associated with each base concept. As an example and not by way of limitation, for multiple base concepts covering cardiovascular issues, each base concept may have similar sub-concepts corresponding to secondary conditions that will affect treatment, e.g. high blood pressure, diabetes, etc. The relationships between each base concept 610 and sub-concepts 622-628 may be stored on a data store of matching-engine system 160. As new base concept+sub-concept combinations are recorded by matching-engine system 160 (e.g. based on newly received episodes of care), the relationship data store may be updated.

Figure 6B:
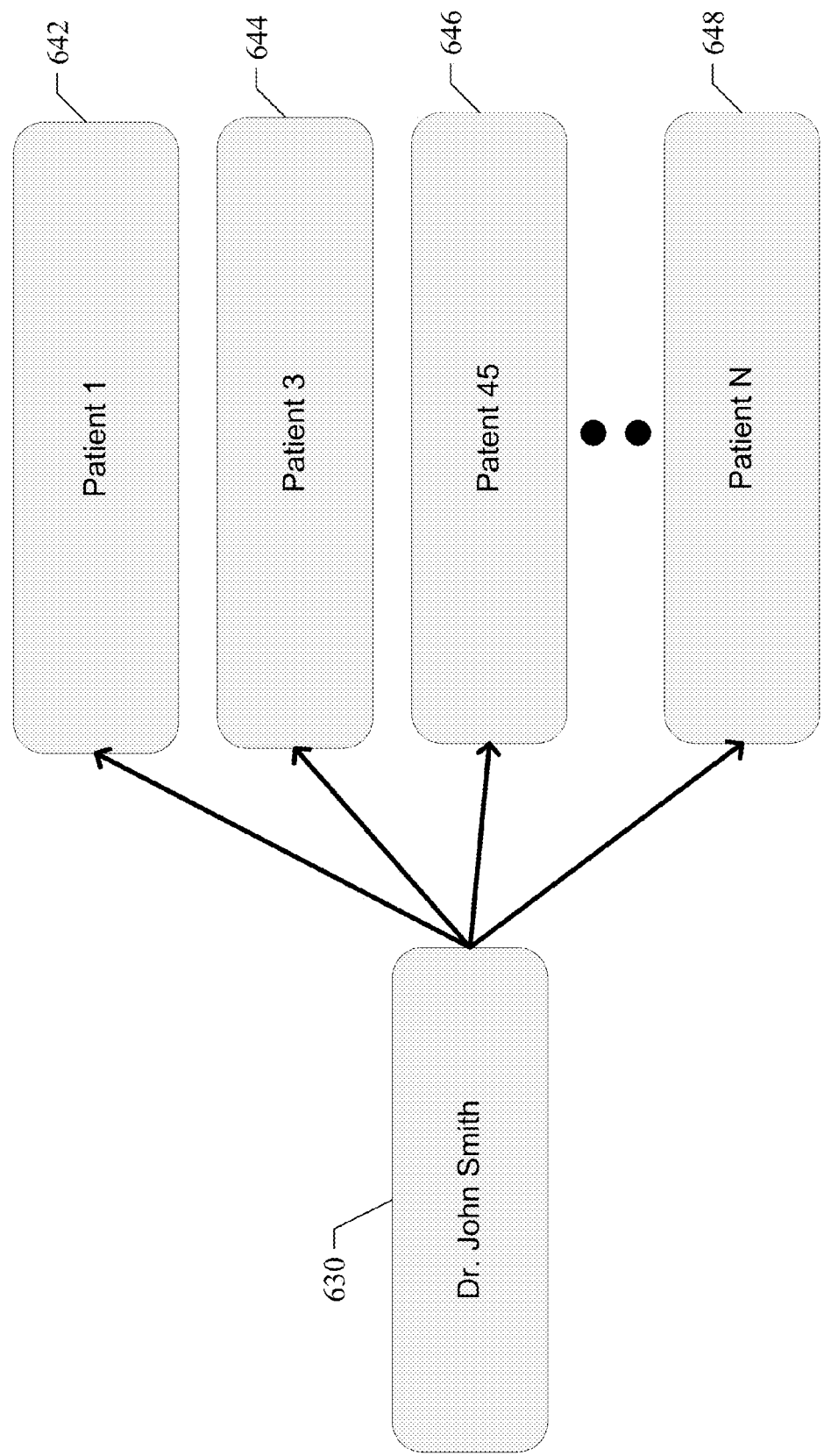
FIG. 6B illustrates an example embodiment of a performance engine matching a physician with one or more patients.

FIG. 6B illustrates an example embodiment of the performance engine which considers one or more patients 642-648 who have visited a particular physician 630 for an episode of care with base concept 610. In particular embodiments, the set of one or more patients 642-648 may represent all patients recorded for physician 630 with respect to base concept 610. In particular embodiments, matching-engine system 160 may consider a subset of patients 642-648 based on time. As an example and not by way of limitation, matching-engine system 160 may only consider patients 642-648 who have made at least one visit to physician 630 in relation to the episode of care within the last six months. In particular embodiments, as new patients come to visit physician 630 in relation to base concept 610, new patients 642-648 may be added.

Figure 6C:
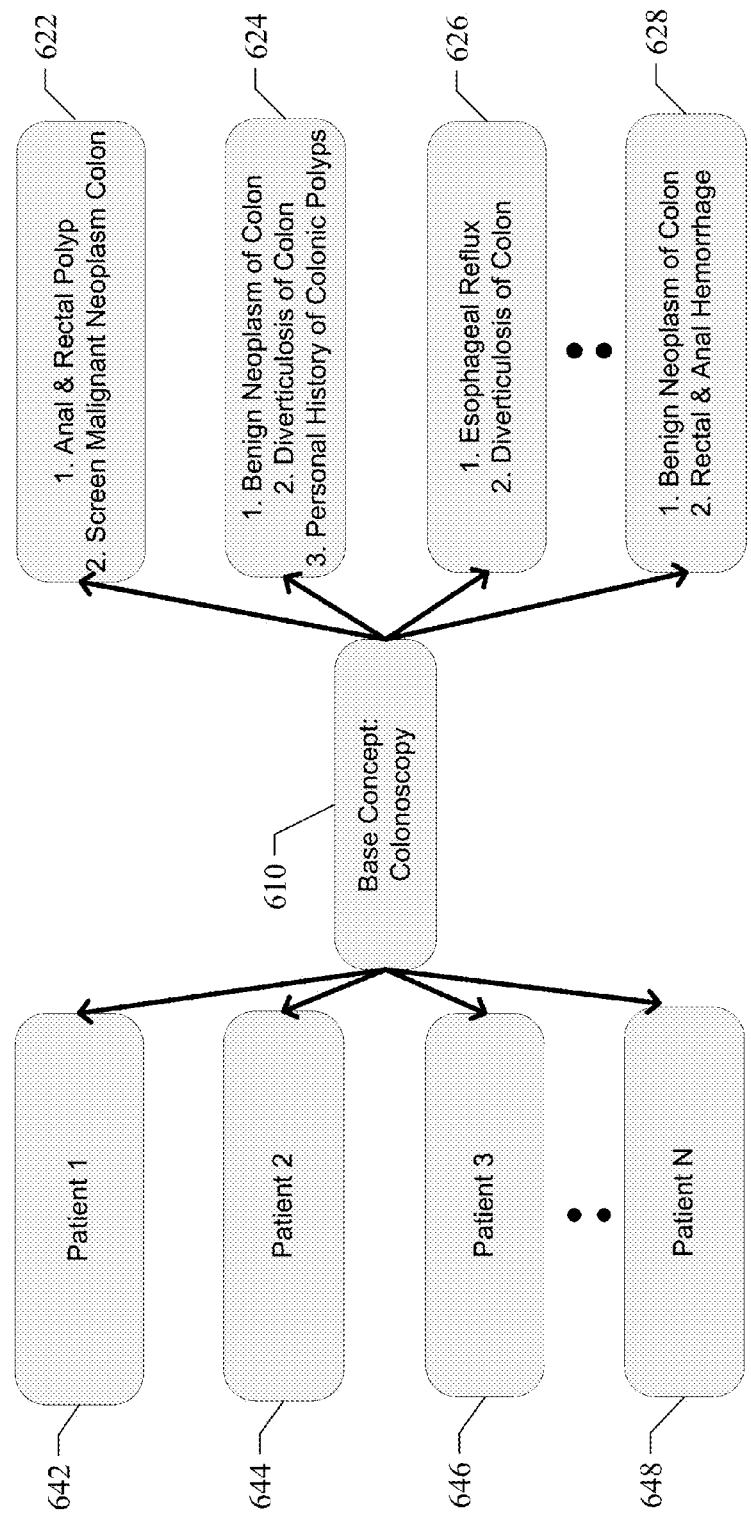
FIG. 6C illustrates an example embodiment of a performance engine matching one or more patients of a base concept with corresponding sub-concept groups.
Figure 6D:
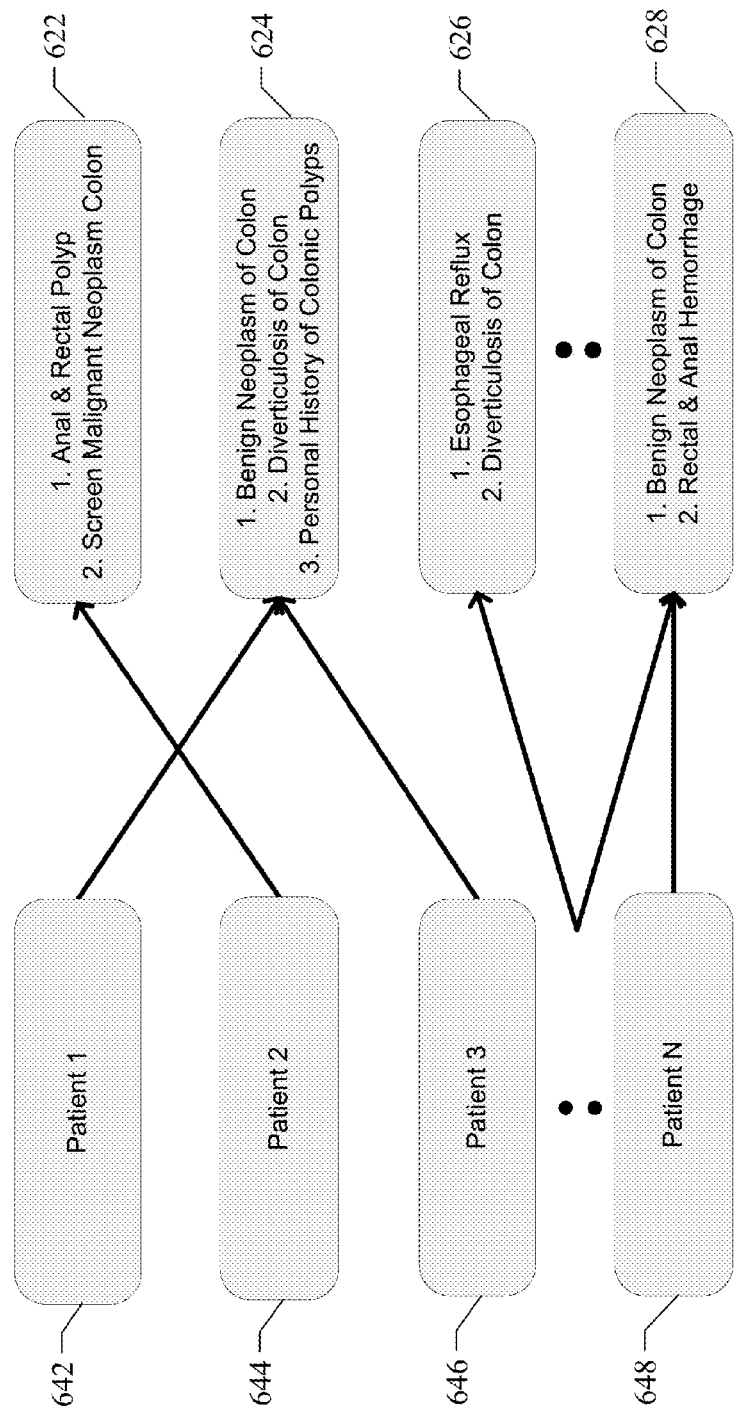
FIG. 6D illustrates an example embodiment of a performance engine matching one or more patients of a base concept with corresponding sub-concept groups.
Figure 6E:
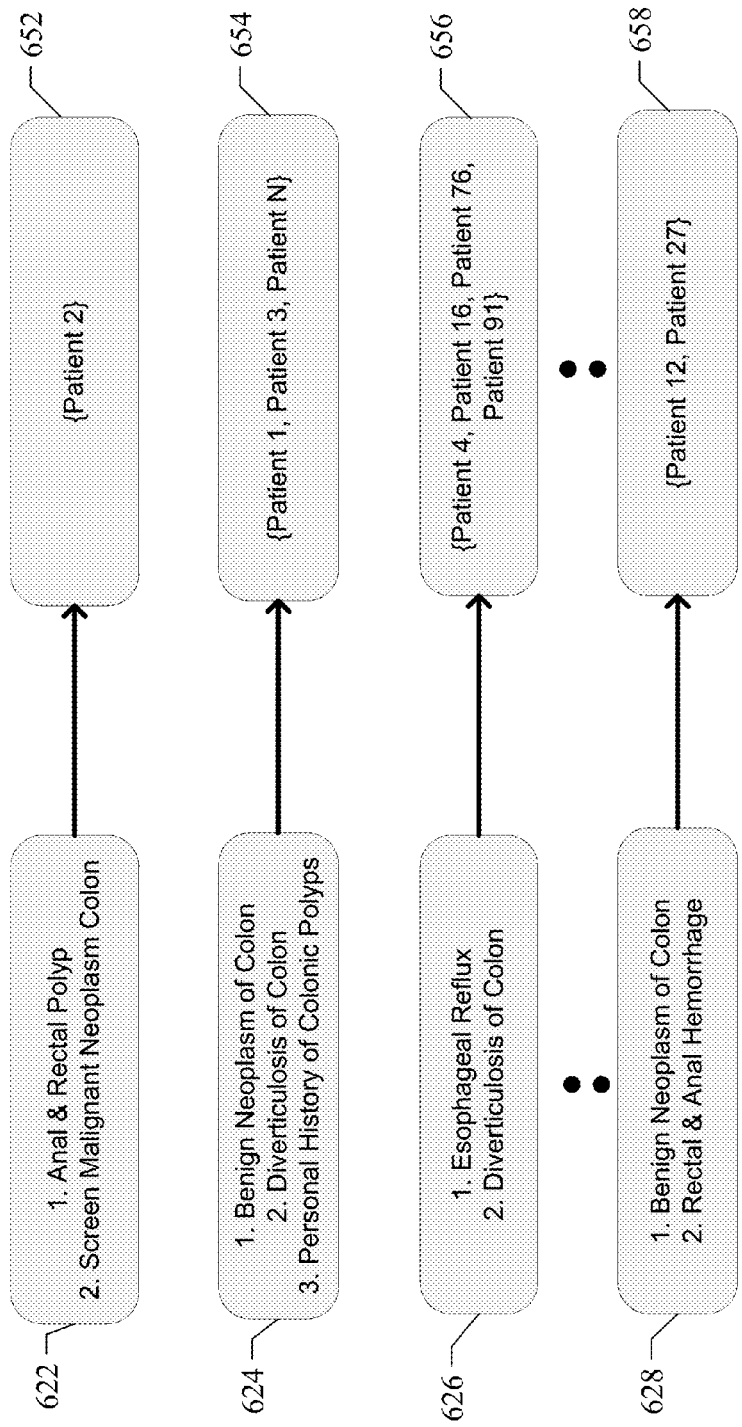
FIG. 6E illustrates an example embodiment of a performance engine matching sub-concept groups with corresponding patient groups.

FIGS. 6C, 6D, and 6E illustrate an example embodiment of the performance engine wherein each patient 642-648 is associated with one or more sub-concept groups 622-628 for the base concept 610. In particular embodiments, matching-engine system 160 may correlate a patient to the sub-concepts based on the CPT codes and ICD codes received from the health-care provider with respect to the particular patient. In particular embodiments, a physician or a health-care provider may provide an indication of one or more sub-concepts to matching-engine system 160. In particular embodiments, each patient 642-648 may be associated with a single sub-concept group 622-628, wherein each sub-concept group represents a distinct group of one or more sub-concepts, i.e. secondary conditions. In particular embodiments, each sub-concept group 622-628 may be associated with one or more patients 642-648. In the example of FIG. 6E, each sub-concept group 622-628 is associated with a patient group 652-658, wherein each patient group 652-658 comprises all patients 642-648 who have the associated sub-concept group 622-628.

Figure 6F:
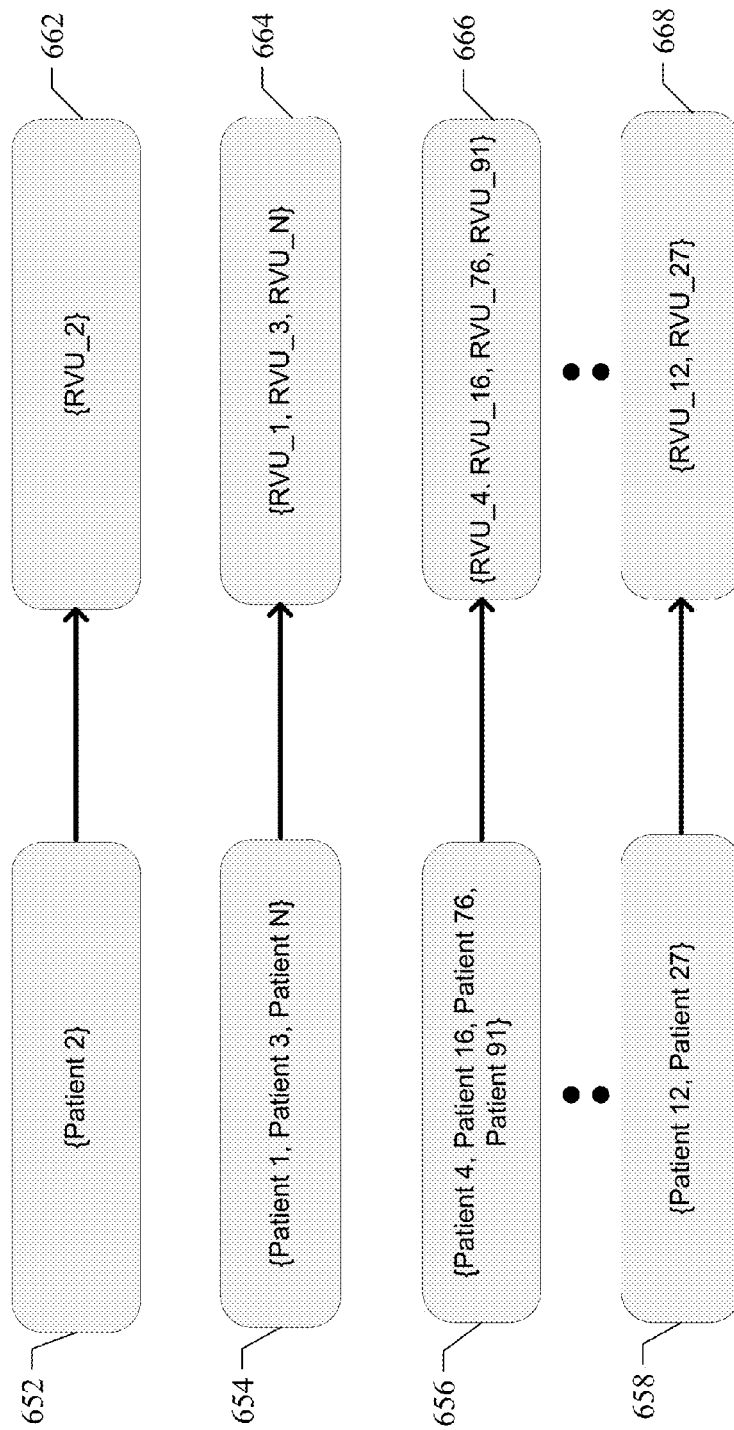
FIG. 6F illustrates an example embodiment of a performance engine matching patient groups with corresponding RVU groups.
Figure 6G:
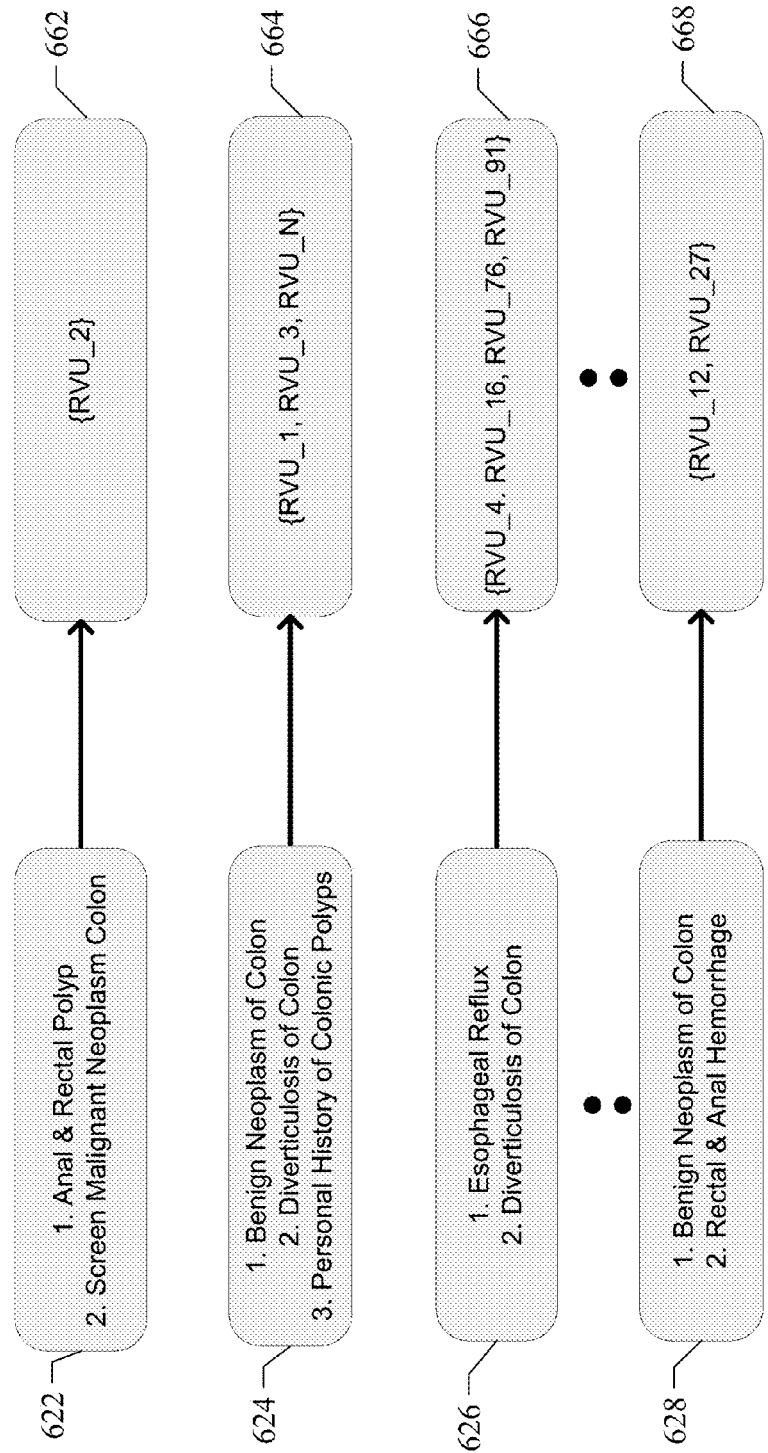
FIG. 6G illustrates an example embodiment of a performance engine matching sub-concept groups with corresponding RVU groups.

FIGS. 6F and 6G illustrate an example embodiment of the performance engine wherein the total RVU costs for each patient are averaged for each patient group 652-658 corresponding to sub-concept groups 622-628. In particular embodiments, the RVU costs for a single patient may be determined by the CPT codes sent with respect to the particular patient during the time of the episode of care. As an example and not by way of limitation, if an episode of care comprises four office visits, each visit having three CPT codes associated with them, then all twelve CPT codes associated with the episode of care may be included. In particular embodiments, as discussed above other cost factors may be included as a part of RVU, such as the actual monetary cost, non-physician services, administrative costs, or costs relating to time or number of patient visits. In the example of FIG. 6F, the total RVU costs for each patient may be included in RVU groups 662-668 corresponding to patient groups 652-658. The value for each RVU group 662-668 may represent an average value of the individual RVU costs for each patient in the group. In the example of FIG. 6G, the RVU groups 662-668 may be correlated with their respective sub-concept groups 622-628. In particular embodiments, the average RVU cost may be a weighted average, with patients seen more recently being weighted more heavily than patients seen during an earlier period of time.

Figure 6H:
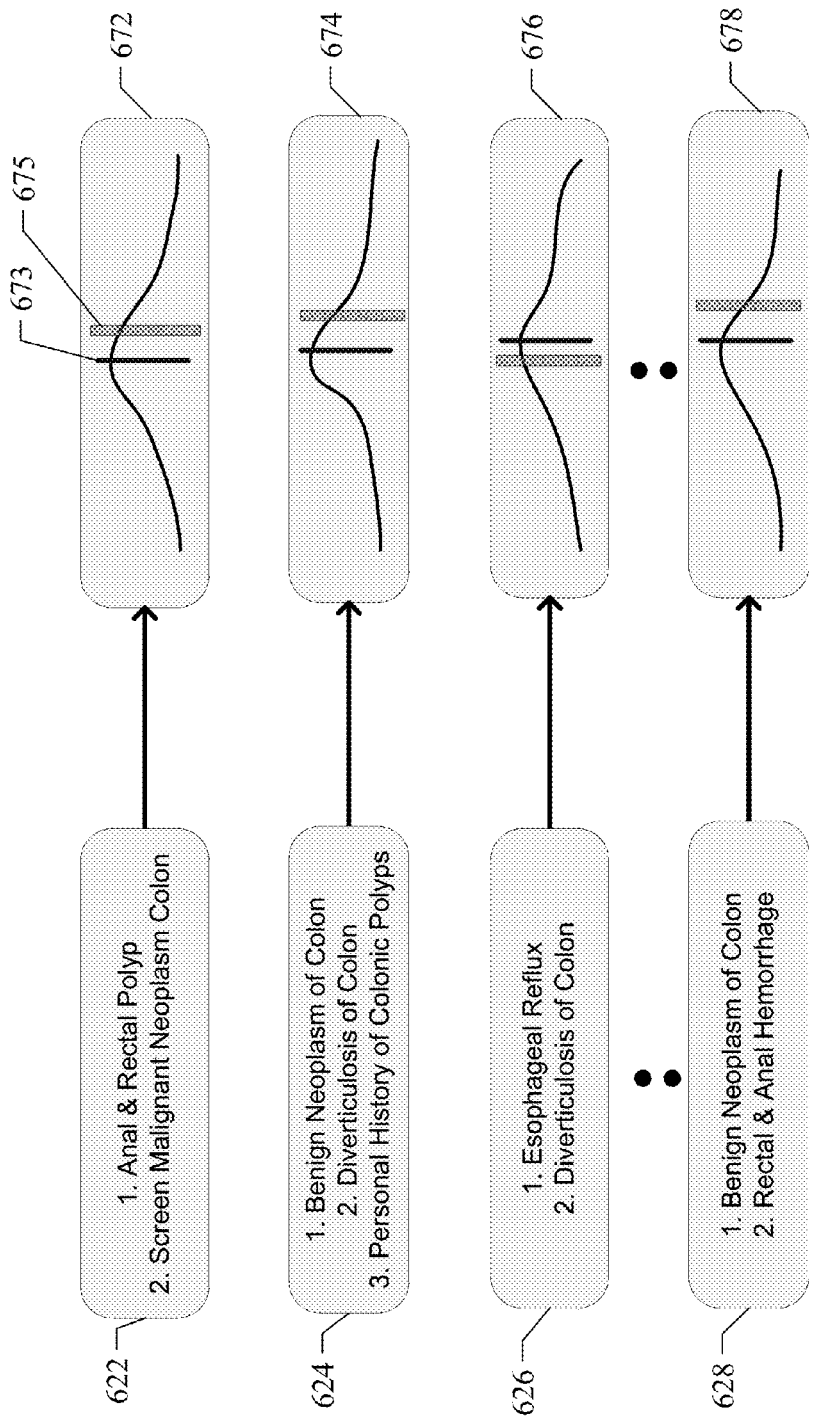
FIG. 6H illustrates an example embodiment of a physician's RVU for one or more sub-concepts compared with the distribution of RVU costs for a peer group of the physician.

FIG. 6H illustrates an example embodiment of the performance engine comparing the RVU groups for a particular physician with the RVU group costs for the peer group of physicians. As discussed above, the peer group of physicians may comprise all physicians in the same specialty and geographic region as the particular physician. In particular embodiments, matching-engine system 160 may calculate the RVU group costs 662-668 for each physician in the peer group. Based on the RVU group costs for each physician, matching-engine system 160 may calculate a distribution of RVU costs 672-678 for the peer group of physicians. The distributions 672-678 may indicate the variation in RVU costs for physicians in treating the particular base concept 610 and sub-concept groups 622-628. In particular embodiments, matching-engine system 160 may calculate the mean RVU cost for the peer group. In the example of FIG. 6H, for distribution 672, line 673 may represent the mean RVU cost for the peer group of physicians comprising distribution 672. In particular embodiments, the mean RVU cost may be weighted by the number of patients seen by each of the peer group physicians. As an example and not by way of limitation, if Dr. Paul has seen 5 patients for base concept 610 with sub-concept group 624, and Dr. Quinn has seen 50 patients for the same base concept 610 and sub-concept group 624, matching-engine system 160 may weight the average RVU cost for Dr. Quinn more greatly than the average RVU cost for Dr. Paul in determining the average RVU cost for the peer group. In particular embodiments, in order to determine the performance score for the particular physician, the average RVU cost for the particular physician may be compared against the distribution and mean of the peer group. In the example of FIG. 6H, line 675 may represent the particular physician's RVU costs for patients in that sub-concept group. In particular embodiments, the performance score may be based on the distance between the physician's RVU cost 675, and the mean RVU cost 673. In particular embodiments, the distance may be represented in units of standard deviations of the distribution 672 from the mean RVU cost 673. In particular embodiments, if a particular physician's individual RVU is more efficient (e.g. lower-cost) than the peer group, the performance score may be positive; if the individual RVU is less efficient (higher costs), then the performance score may be a negative value.

In particular embodiments, matching-engine system 160 may then determine a set of performance scores for each sub-concept group 622-628, wherein each performance score corresponds to the difference between the particular physician's RVU costs within the sub-concept group, compared to the average RVU costs of the peer group. In particular embodiments, matching-engine system 160 may then aggregate the individual performance scores into a total performance score for a particular base concept 610. In particular embodiments, matching-engine system 160 may weight each performance score based on the number of patients the particular physician has treated with the underlying sub-concept group. The aggregate performance score may then be calculated as a weighted average. As an example and not by way of limitation, if Dr. Tina has a performance score of 0.5 in sub-concept group 622 with ten patients seen, and has a performance score of 2.5 in sub-concept group 624 with twenty patients seen, then matching-engine system 160 may calculate the aggregate performance score to be ((0.5*10)+(2.5*20))/30=2.00.

In particular embodiments, matching-engine system 160 may calculate a weighted average for the aggregate performance score based on the number of patients seen by the peer group of physicians for each sub-concept type. This may reflect the overall likelihood that a user seeking a physician within the base concept has a particular sub-concept type. As an example and not by way of limitation, matching-engine system 160 may determine in the example above that a total of 100 patients were treated by physicians in Dr. Tina's peer group with sub-concept group 622, and a total of 50 patients were treated with sub-concept group 624. In this example, if a new user is seeking treatment for the same base concept, matching-engine system 160 may determine that a user is twice as likely to have sub-concept group 622 as 624. The weighted average aggregate performance score in this example for Dr. Tina may then be ((0.5*100)+ (2.5*50))/150=1.167.

Experience Index

In particular embodiments, matching-engine system 160 may consider the experience index of physicians in generating or ranking the set of physicians for recommendation to the user. An experience index may represent the overall experience of a physician in dealing with a particular type of conditions or diseases, beyond a mere count of patients who have visited the physician. In particular embodiments, an experience index may also account for relative case volume, case severity, and variety seen by the physician. In particular embodiments, the experience index may be localized to be evaluated against physicians within a given state; within a given MSA; within a specialty class within the MSA; within a specialization within the specialty class; and within a condition group within the specialization based on diagnoses and procedure codes. In particular embodiments, using a localized context for the experience index may allow for a very homogenous context of analysis, may allow for environmental and population health factors to be included in the analysis, and may narrow the context of the analysis. The experience index is calculated using only provider-reported insurance claims data, and thus will be free of any subjective reviews from patients. Another advantage to the experience index may be that because it is calculated by comparing providers to each other, just two providers in the same specialization in the same locality are needed to calculate the experience index.

Figure 7:
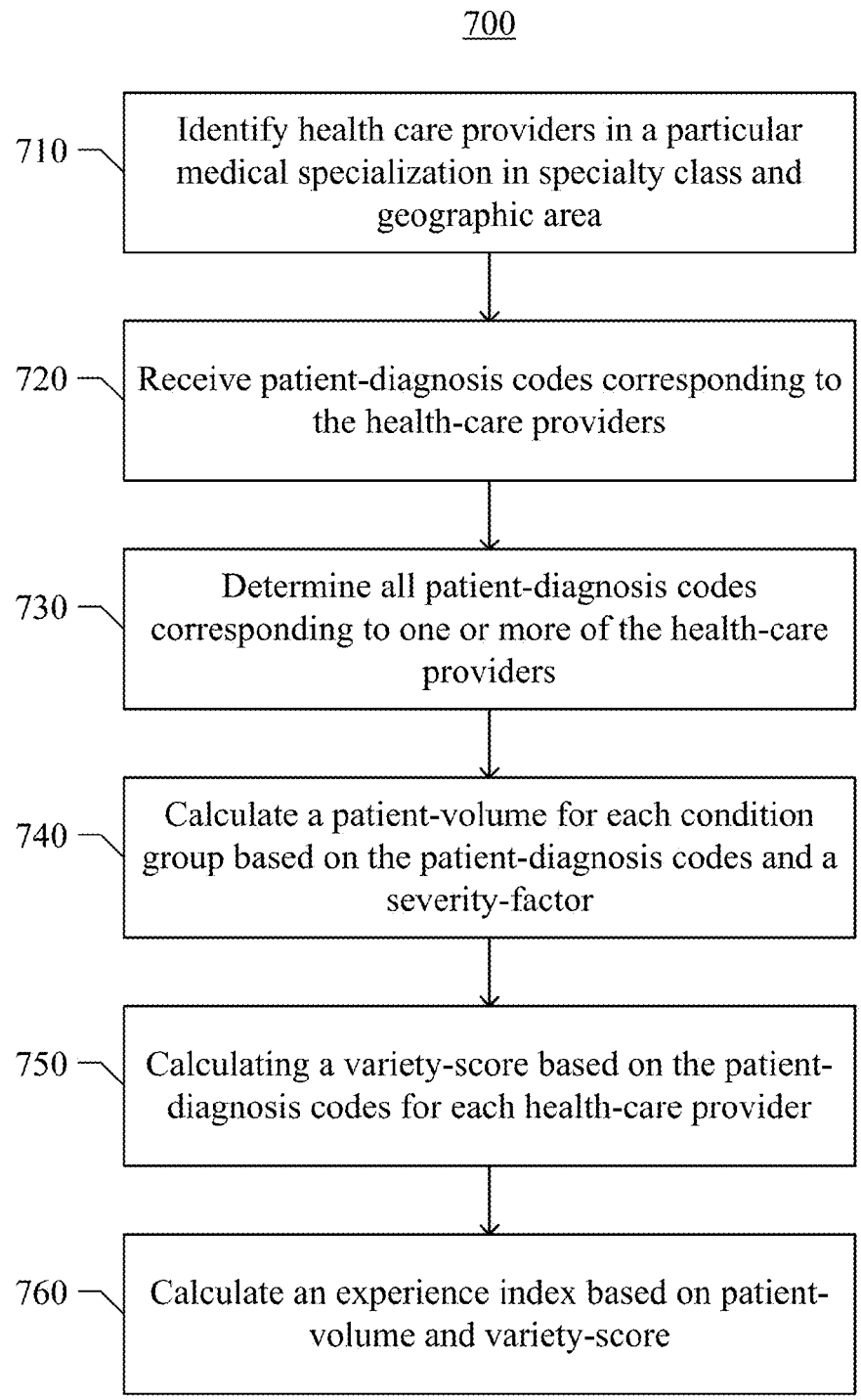
FIG. 7 illustrates an example method of calculating an experience index for a physician.

FIG. 7 illustrates an example method of calculating an experience index for a particular physician. The method may begin at step 710, where matching-engine system 160 may identify all health-care providers or physicians within a particular specialization in a specialty class and geographic area. As an example and not by way of limitation, a specialization may be cardiology within a specialty class of internal medicine. In particular embodiments, the geographic area may be an MSA within a particular state. At step 720, matching-engine system 160 may receive patient-diagnosis codes corresponding to the identified health-care providers. As an example and not by way of limitation, patient-diagnosis codes may comprise ICD codes submitted by the providers on insurance claims. In particular embodiments, the patient-diagnosis codes may correspond to one or more condition groups. Each condition group may represent a similar group of conditions or diseases. At step 730, matching-engine system 160 may determine all patient-diagnosis codes corresponding to one or more of the providers. In particular embodiments, this step may comprise determining all patient-diagnosis codes within a particular condition group for a provider. In particular embodiments, each patient-diagnosis code received by matching-engine system 160 may further comprise a severity index which represents whether the underlying instance of the condition for the patient-diagnosis code was non-chronic or chronic.

At step 740, matching-engine system 160 may calculate a patient-volume for a particular condition group for a provider based on the received patient-diagnosis codes and the corresponding severity factors. In particular embodiments, the volume of patients may be a relative measure of how many patients a particular provider saw compared to the rest of the identified providers. As an example and not by way of limitation, in a condition group for cardiac dysrhythmias, a total group of providers may have seen 100 patients with chronic cases, and 200 patients with non-chronic cases. Within the group of providers, Dr. Alex may have seen 20 of the chronic cases, and 30 of the non-chronic cases. In this example, the case volume for Dr. Alex would be 20/100=0.20 for chronic cases of cardiac dysrhythmia, and 30/200=0.15 for non-chronic cases. The two case volumes may be combined by adjusting for case severity. In particular embodiments, chronic cases may be multiplied by an additional factor. As an example and not by way of limitation, chronic cases may be deemed to require three times as many resources as non-chronic cases. Therefore, chronic case volume may be weighted three times as much as non-chronic cases. In the example above, Dr. Alex may have a severity-normalized case volume of (0.20×3+0.15)/(3+1)= 0.1875. A higher normalized case volume may indicate that the particular provider has seen more overall cases in the condition group, and/or more severe cases compared to their peers.

At step 750, matching-engine system 160 may also calculate a variety score for the group of health-care providers. In particular embodiments, the variety score may represent the number of types of diseases seen by a particular provider within a specialization. Matching-engine system 160 may determine a total variety of conditions by determining the number of distinct patient-diagnosis codes submitted by all identified providers within a specialization. As an example and not by way of limitation, matching-engine system 160 may receive fifty different patient-diagnosis codes from cardiologists within the Denver, Colo. MSA. Using only the distinct conditions seen within the geographic region may adjust the variety for the population health, e.g. if no one in the MSA has a particular condition within the condition group. Matching-engine system 160 may then determine the number of distinct patient-diagnosis codes seen by a particular provider. In this example, if Dr. Jones, a cardiologists from Denver, has seen forty distinct conditions with their own patient-diagnosis codes, matching-engine system 160 may determine that Dr. Jones' variety score is 40/50=0.8. In particular embodiments, the variety score may be calculated based on the number of condition groups within a specialization are seen by one provider versus the entire group of providers.

At step 760, matching-engine system 160 may calculate an experience index based on the severity-normalized case volume and the variety score. In particular embodiments, the experience index may be the product of the severity-normalized case volume and the variety score. In particular embodiments, the experience index may be a weighted sum or average of the severity-normalized case volume and the variety score. As an example and not by way of limitation, a weighted average may be used if matching-engine system 160 determines that the normalized case volume is more indicative of a physician's experience than the variety of cases the physician has seen.

Particular embodiments may repeat one or more steps of the method of FIG. 7, where appropriate. Although this disclosure describes and illustrates particular steps of the method of FIG. 7 as occurring in a particular order, this disclosure contemplates any suitable steps of the method of FIG. 7 occurring in any suitable order. Moreover, although this disclosure describes and illustrates particular components, devices, or systems carrying out particular steps of the method of FIG. 7, this disclosure contemplates any suitable combination of any suitable components, devices, or systems carrying out any suitable steps of the method of FIG. 7.

Figure 8A:
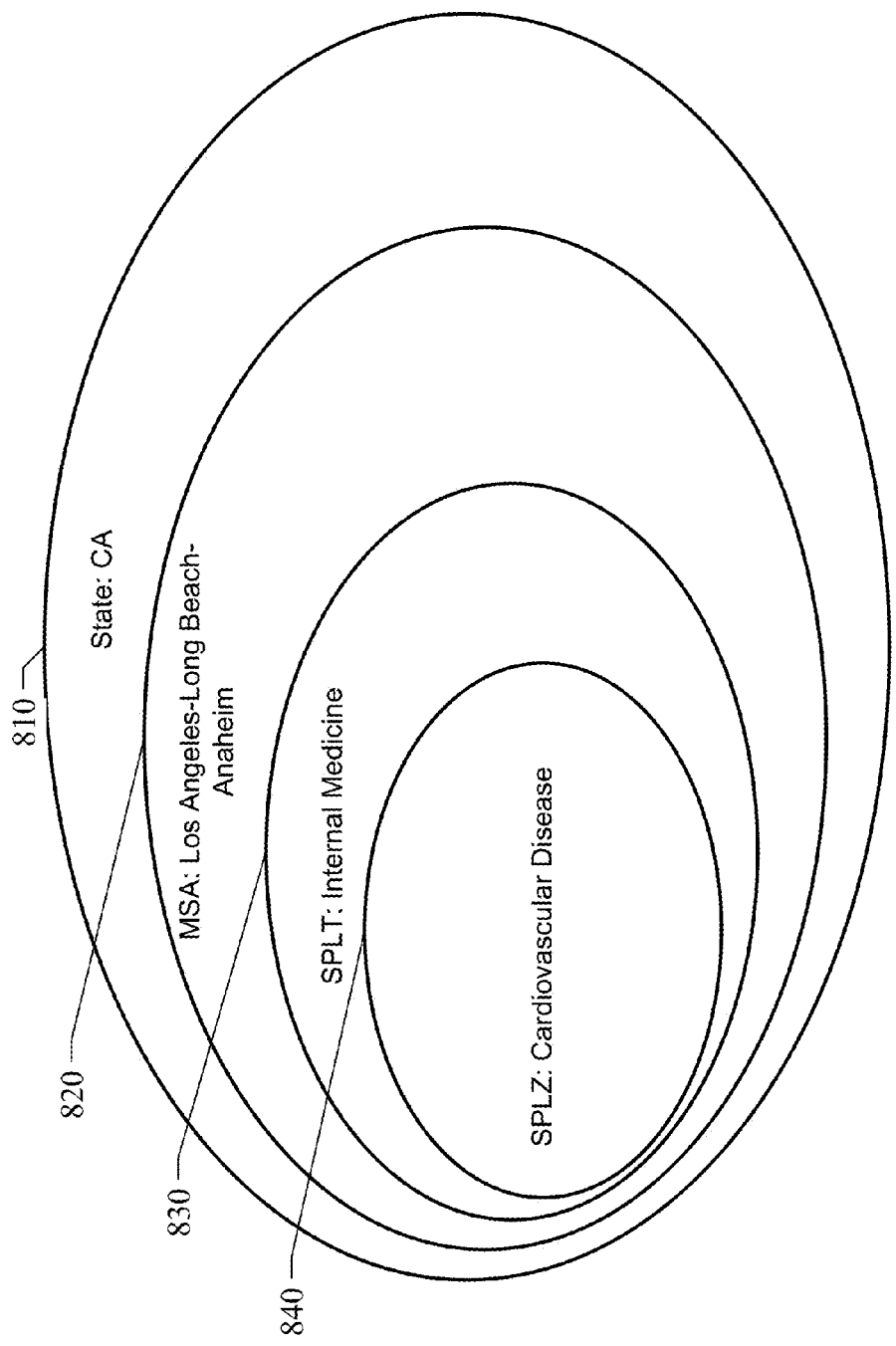
FIG. 8A illustrates an example embodiments of an experience engine determining a group of physicians based on specialization and geographic area.
Figure 8B:
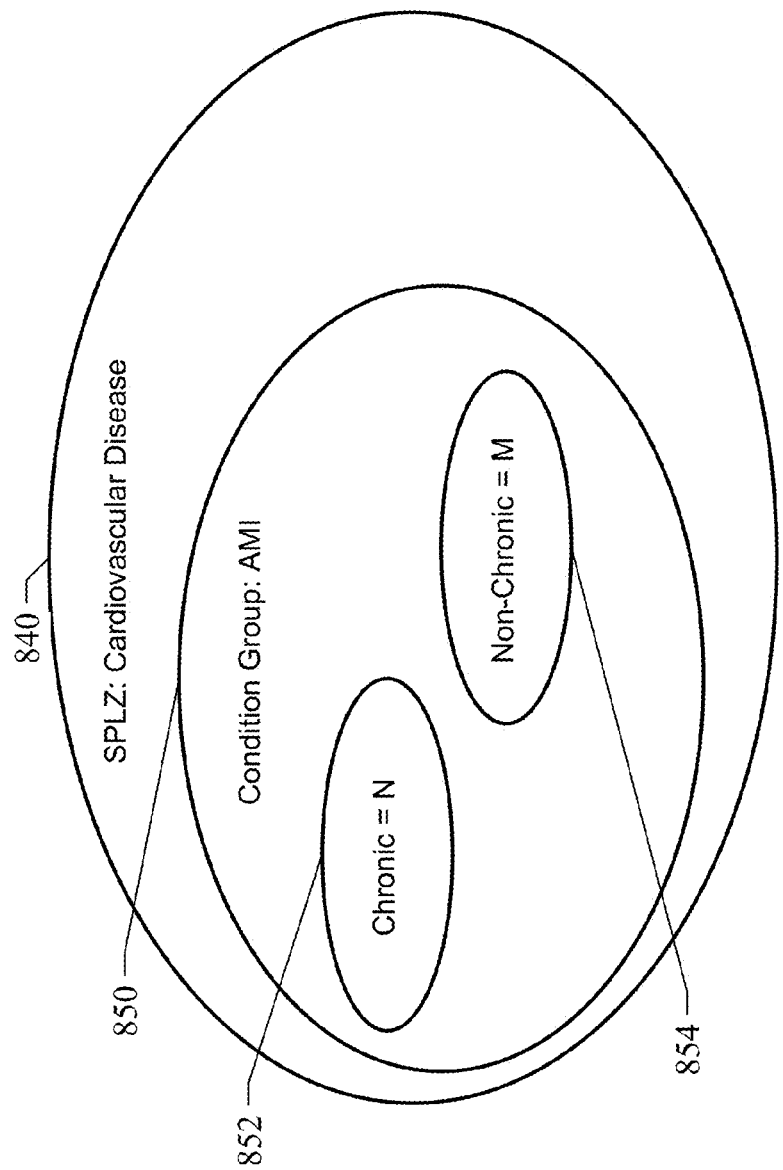
FIG. 8B illustrates an example embodiment of an experience engine determining a case volume for a particular specialization.

FIGS. 8A-8B illustrate example embodiments of the experience engine of matching-engine system 160. In the example of FIG. 8A, matching-engine system 160 may identify health-care providers or physicians within a particular specialization 840, within a particular specialty class 830, within a particular metropolitan statistical area (MSA) 820 within a state 810. The providers belonging to this narrowed group of specialists by specialization 840 may comprise a peer group of providers to determine the relative case volume and case variety for one of the providers. In the example of FIG. 8B, the number of cases within a particular condition group 850 may be identified within the specialization 840. Within condition group 850, matching-engine system 160 may identify a number of chronic cases 852, as well as a number of non-chronic cases 854. In particular embodiments, the number of cases 852 and 854 may be for a specific provider within specialization 840. In particular embodiments, the number of cases 852 and 854 may be for all providers within specialization 840. As discussed above, the ratio of cases seen by one provider may be compared to the number of cases seen by all providers to calculate a relative case volume, which may be normalized by case severity.

Figure 8C:
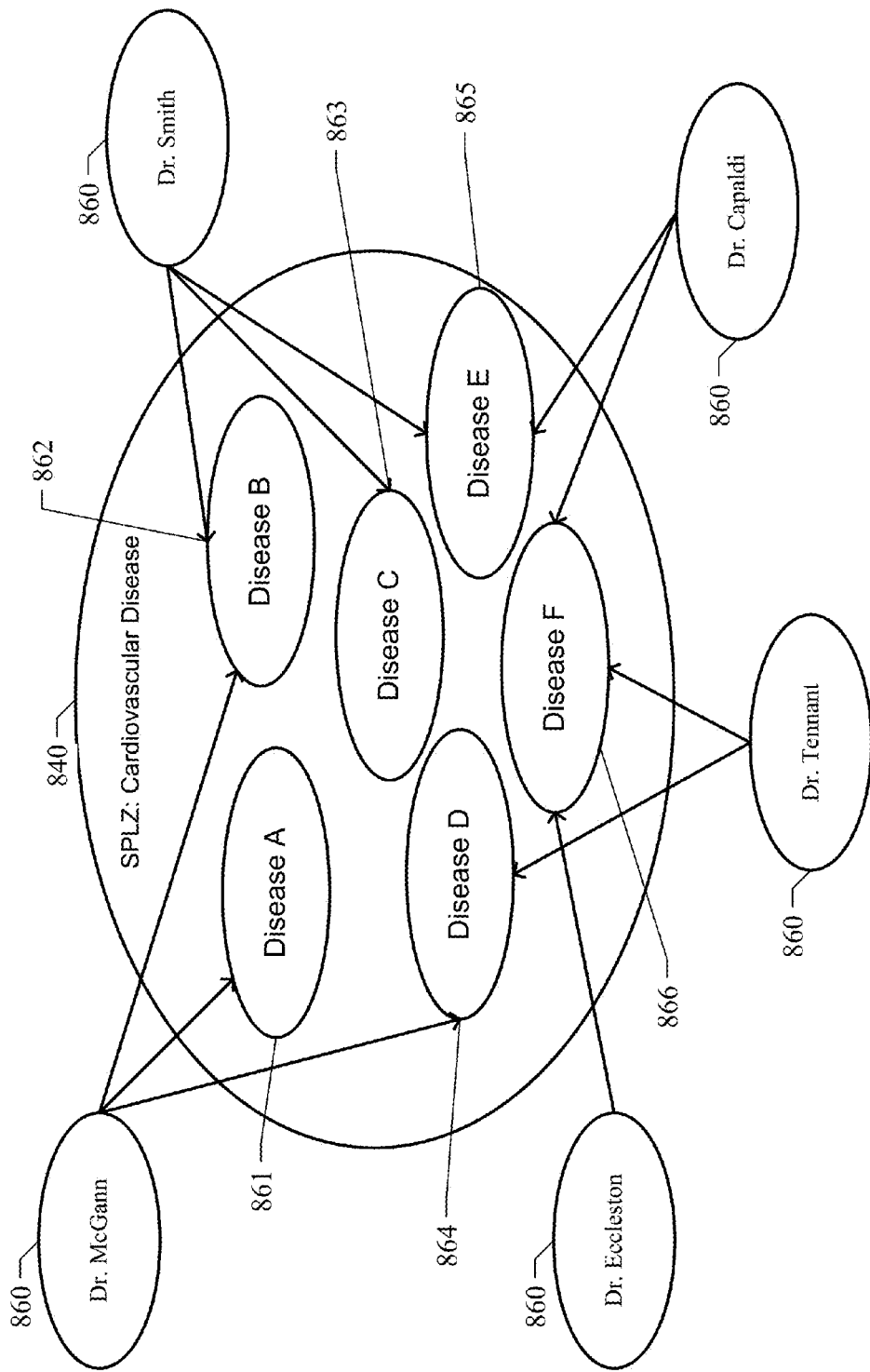
FIG. 8C illustrates an example embodiment of an experience engine determining a variety-score for physicians in a specialization.

FIG. 8C illustrates an example embodiment of determining a variety score. In this example, specialization 840 may comprise five physicians 860. Over a predetermined period of time, these physicians 860 may have diagnosed patients with six distinct conditions 861-866. Each of the conditions 861-866 may comprise a different condition group; or matching-engine system 160 may calculate variety based on distinct conditions within a condition group. Matching-engine system 160 may compare the number of conditions seen by each physician versus the total number of conditions seen by the group. In the example of FIG. 8C, Dr. McGann has seen three conditions; Dr. Eccleston has seen one; Dr. Tennant has seen two; Dr. Capaldi has seen two; and Dr. Smith has seen three. Matching-engine system 160 may divide each of these numbers by the total number of conditions for this specialization 840 to obtain variety scores for the five doctors: Dr. McGann and Dr. Smith have variety scores of 0.5; Dr. Eccleston has 0.167; and Dr. Tennant and Dr. Capaldi have variety scores of 0.33. Matching-engine system 160 may use these variety scores in combination with a severity-normalized case volume for each provider to determine the overall experience index.

User Interface

Figure 9:
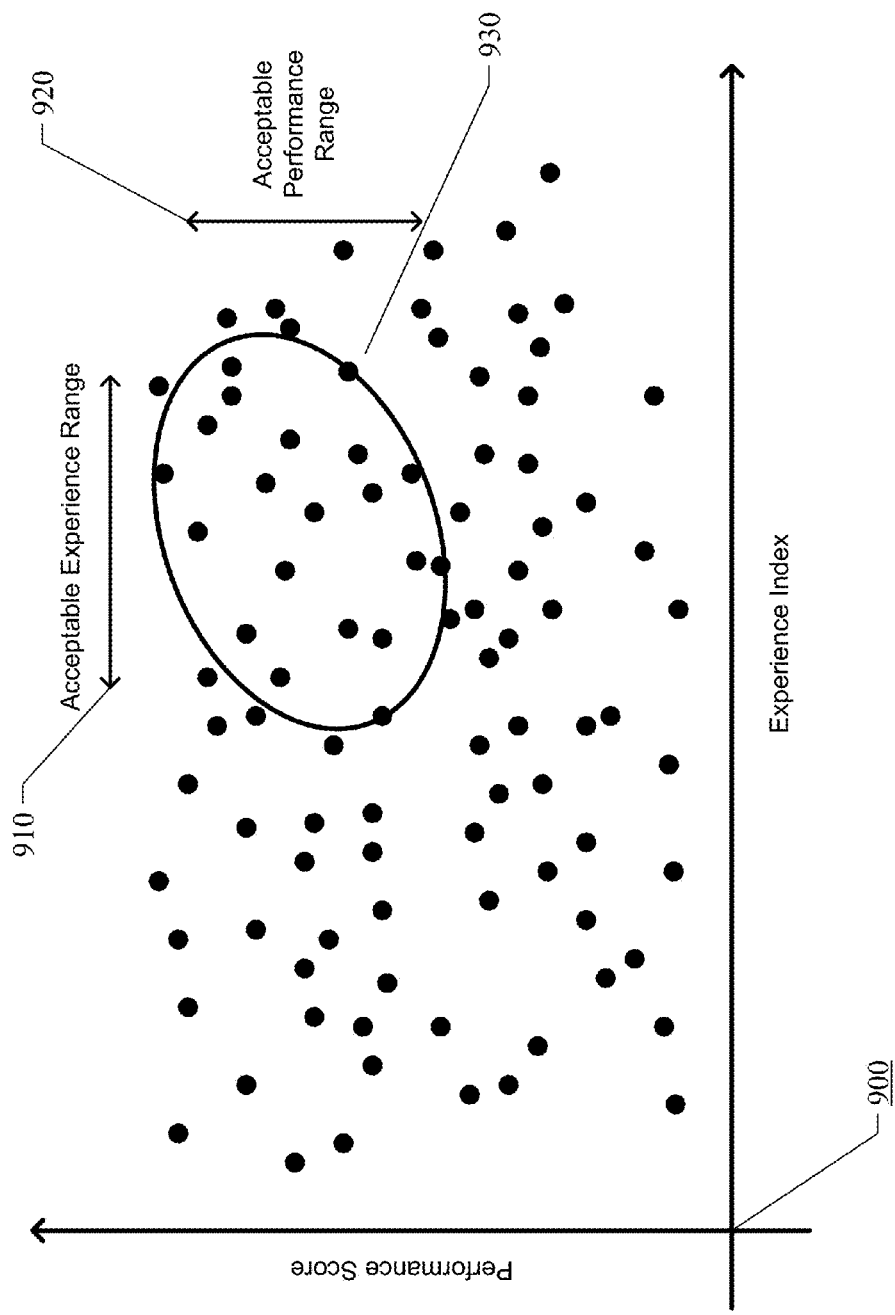
FIG. 9 illustrates an example embodiment of the matching engine selecting a set of physicians based on parameters for performance scores and experience indices.

In particular embodiments, the performance scores and experience index for each physician may be used to determine whether the physician should be recommended to a particular user based on a request sent by that user. FIG. 9 illustrates an example embodiment for selecting one or more physicians for recommendation. Graph 900 show examples of physicians plotted by their respective experience indices and performance scores. In particular embodiments, a single graph like graph 900 may only show the plotted experience indices and performance scores for a particular base-concept. In the example of FIG. 9, graph 900 includes acceptable ranges 910 and 920 for the performance score and experience index, respectively. Acceptable ranges 910 and 920 create a region 930 of data points which are acceptable for recommendation to a user. Matching-engine system 160 may determine that physicians with data points within region 930 are acceptable for recommendation to the user.

Figure 10A:
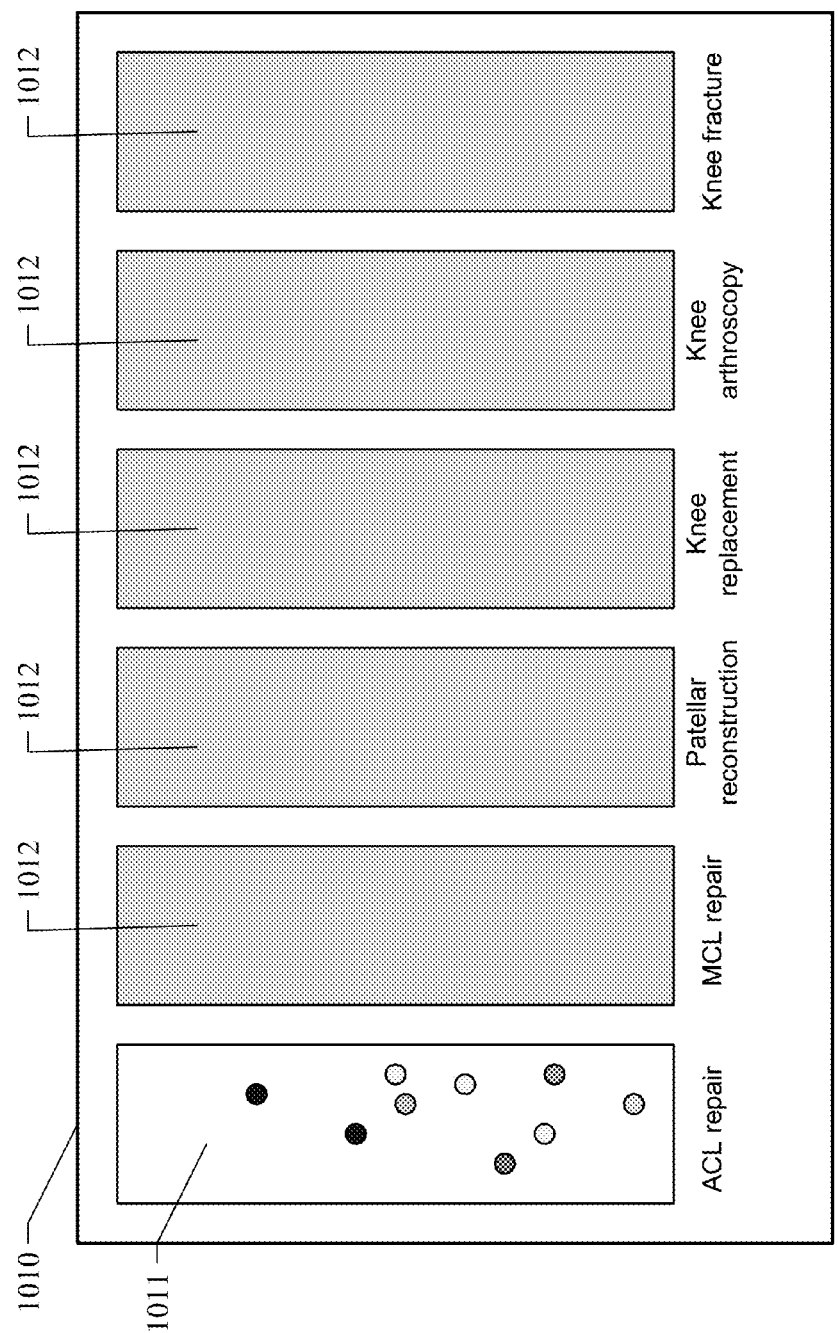
FIG. 10A-10E illustrate example embodiments of a user interface for presenting recommended physicians to a user of a matching engine system.

In particular embodiments, one or more physicians or health-care providers may be recommended to a user submitting a search query. FIG. 10A illustrates an example user-interface 1010 for presenting a set of physicians to the user. In the example of FIG. 10A, a user may be presented with treatment types 1011 and 1012, wherein each treatment type corresponds to a particular treatment, medical condition, or condition-group. The treatment types 1011 and 1012 in the example of FIG. 10A correspond to various types of treatments involving the knee, or a condition regarding the knee. For example, these categories may be presented to a user who input "sharp knee pain." As another example, the user may have specifically searched for "ACL repair," and the other treatment types 1012 may be presented as related searches or categories. The user may interact with treatment types 1011 and 1012 to view more information within the selected treatment type.

Figure 10B:
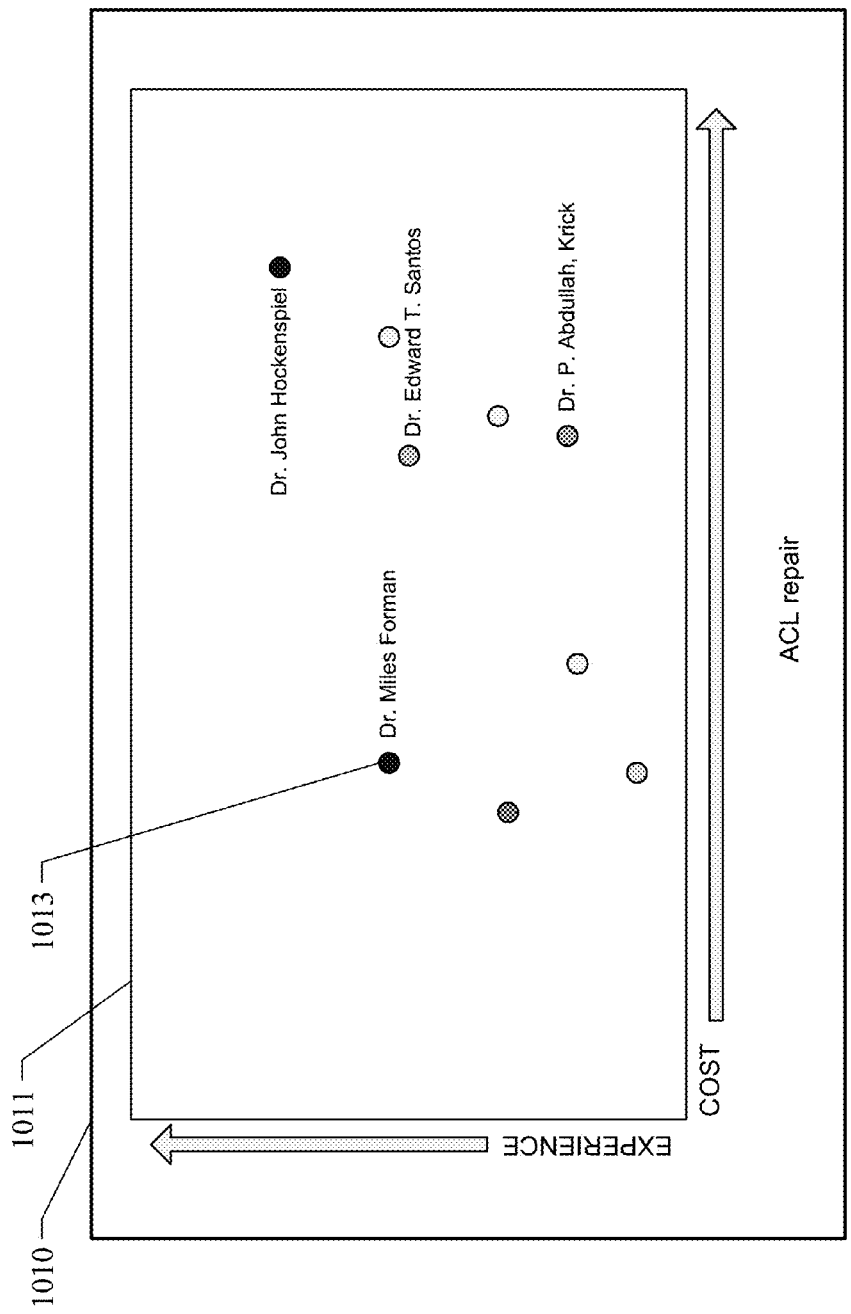
Figure 10C:
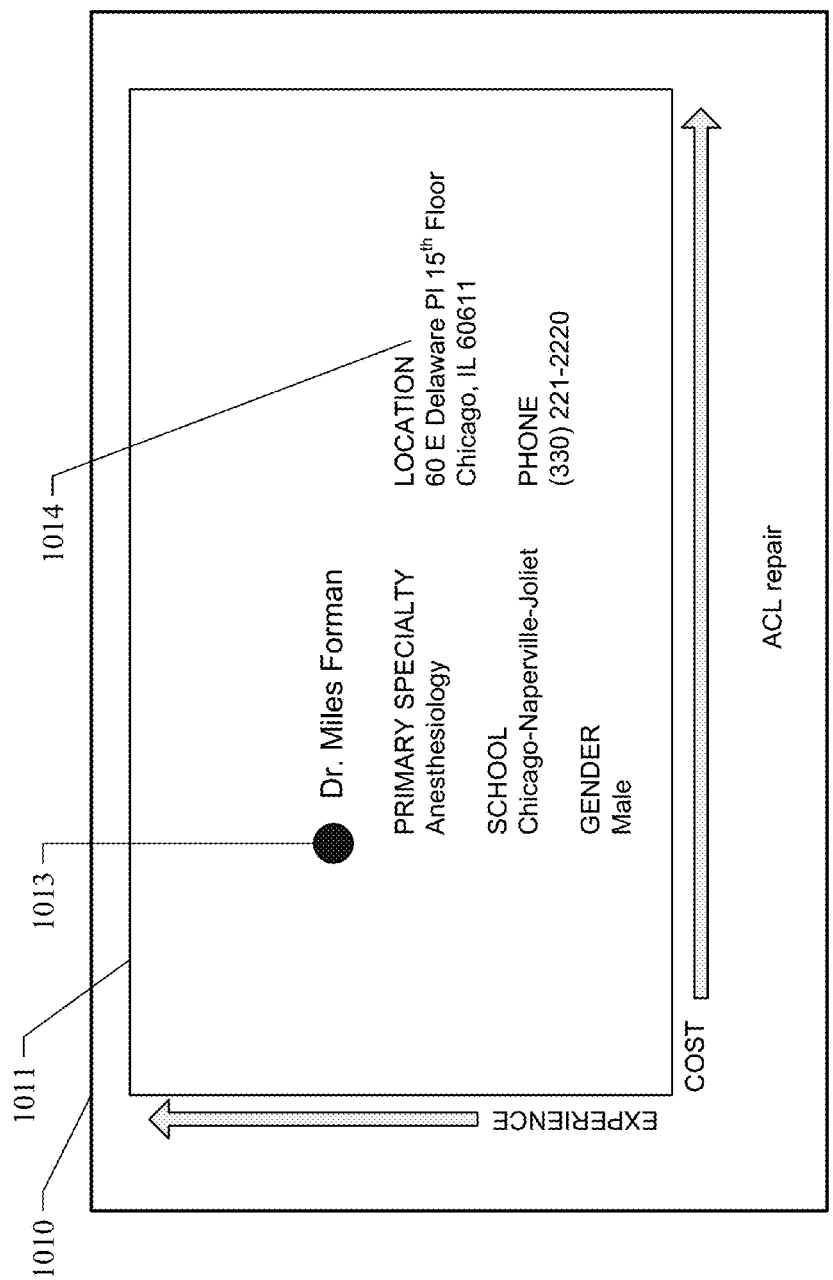

FIG. 10B illustrates an embodiment of the user-interface 1010 of FIG. 10A once treatment type 1011 has been selected by the user. Treatment type 1011 may be expanded to a full graph, wherein the axes of the graph correspond to a cost value of the physician, and the experience of the physician. In particular embodiments, the cost value may correlate to the performance score of the physician. In particular embodiments, the cost value may correlate to the monetary costs corresponding to each physician for services related to treatment type 1011. Each physician 1013 may be represented as a point on the graph, wherein each point's x and y values correspond to the physician's cost value and experience. In particular embodiments, each physician point 1013 may be represented by a shaded region, wherein the intensity of the shading corresponds to the strength of the recommendation. As an example and not by way of limitation, in FIG. 10B, point 1013 corresponding to Dr. Miles Forman is shaded black, which may indicate that Dr. Forman is strongly recommended. Other physician points with lighter shading may correspond to physicians that are not as strongly recommended to the user. In particular embodiments, a user may interact with physician point 1013 to view further information about the physician. FIG. 10C illustrates an example embodiment of user-interface 1010 once a physician point 1013 has been selected. In the example of FIG. 10C, additional physician information 1014 may be presented to the user. In particular embodiments, physician information 1014 may comprise data reflecting reasons why the physician was recommended, such as quantitative measures of experience, cost, or distance from the user.

Figure 10D:
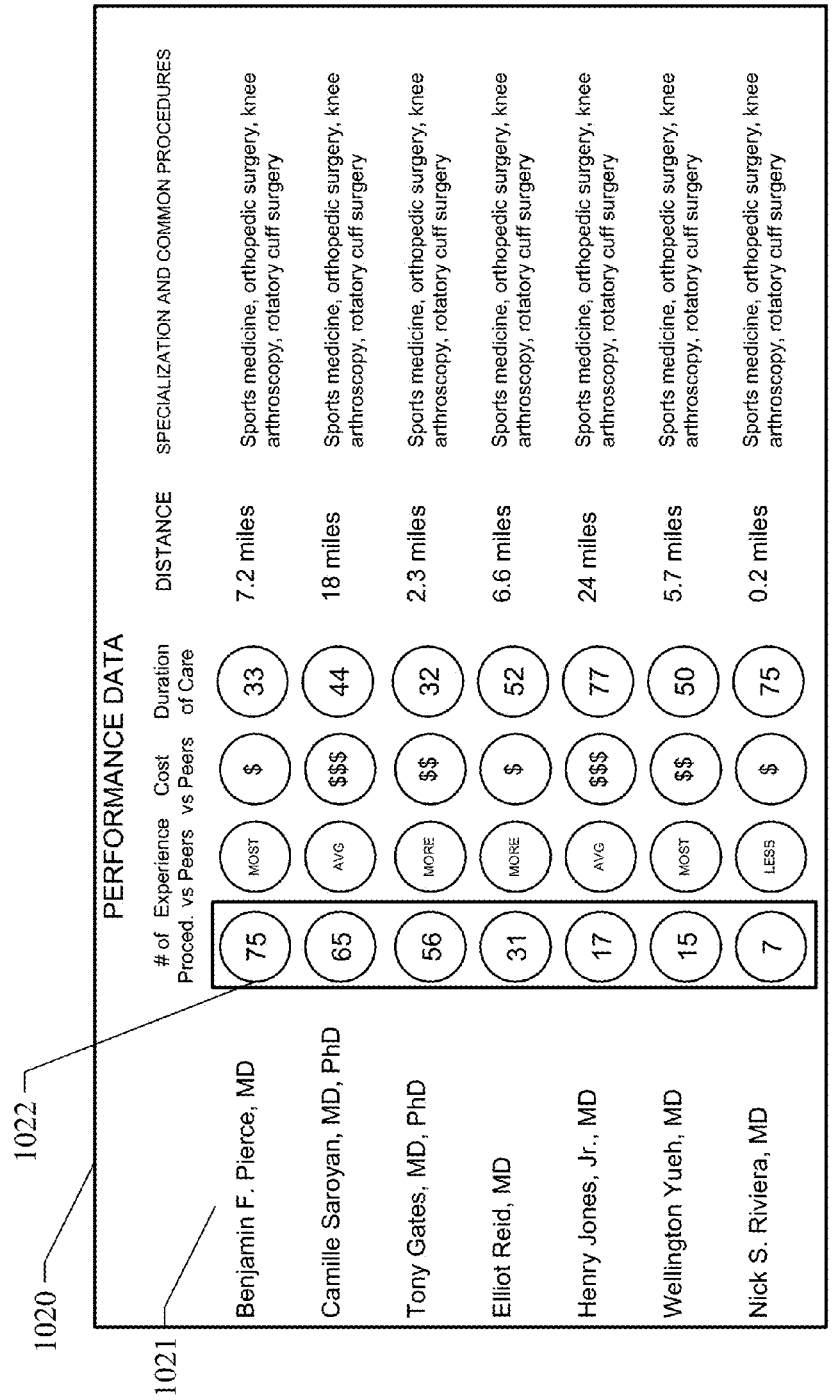

FIG. 10D illustrates an example embodiment of a user-interface 1020 for presenting recommended physicians in a list 1021. In the example of FIG. 10D, a user may view additional information for each physician, and sort the list 1021 by a column 1022. As an example and not by way of limitation, the example of FIG. 10D shows a list 1021 sorted by the number of procedures performed by each physician in column 1022. In particular embodiments, the columns 1022 may display information that is not a corresponding value to the experience index or performance score of the physician. As an example and not by way of limitation, users may not instinctively grasp values such as experience indices or performance scores, but may understand concepts such as "number of procedures performed" and "duration of care." In particular embodiments, the experience index and performance score may be presented in an easily-understood form. As an example and not by way of limitation, in FIG. 10D, the experience index may correspond to the column for "experience vs peers," which only has values for "most," "more," "average," and "less." As another example, the performance score may correspond to the column for "cost vs peers," which is represented by a number of dollar signs.

Figure 10E:
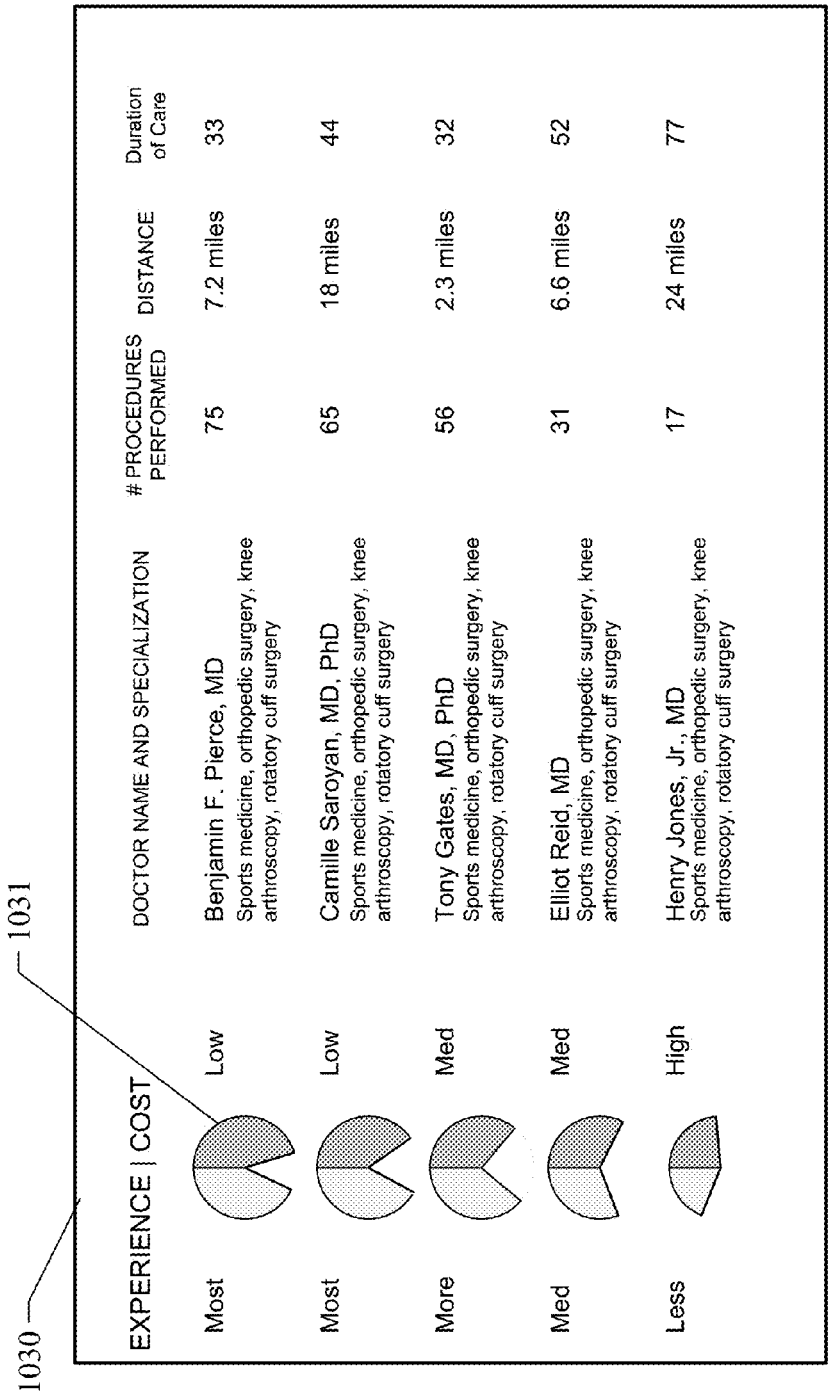

FIG. 10E illustrates another example embodiment of a user-interface 1030 for presenting recommended physicians.

User-interface 1030 displays information substantively identical to user-interface 1020 of FIG. 10D. In the example of FIG. 10E, user-interface 1030 displays the experience of the physician and relative cost in a pie chart format 1031. In this example, more complete sections of the pie chart may correspond to better values for experience and cost.

Referral Network

In particular embodiments, matching-engine system 160 may be able to monitor referrals made by a first physician to a second physician. A first physician may refer a patient to a second physician for further medical services, for example services that are not within the first physician's specialty or a service that the first physician feels the second physician may perform better for the patient. As an example and not by way of limitation, if an internal medicine specialist is treating a patient and diagnoses that the patient has a heart murmur, the internist may refer the patient to a cardiologist for further diagnosis or treatment. The internist may recommend any cardiologist, or may recommend one by name to the patient.

In particular embodiments, matching-engine system 160 may comprise a physician-referral-network which records existing and new referrals made between physicians of the physician-referral-network. In particular embodiments, the physician-referral network may comprise a plurality of nodes and a plurality of edges connecting the nodes, wherein each node corresponds to a physician, and an edge connecting two physician-nodes indicates at least one direct referral between the physicians. In particular embodiments, the edges may comprise information referencing a number of referrals made in either direction between two physicians, and what types of medical services are referenced in the referrals. In particular embodiments, information pertaining to the number and type of referrals may be stored with each node.

Figure 11:
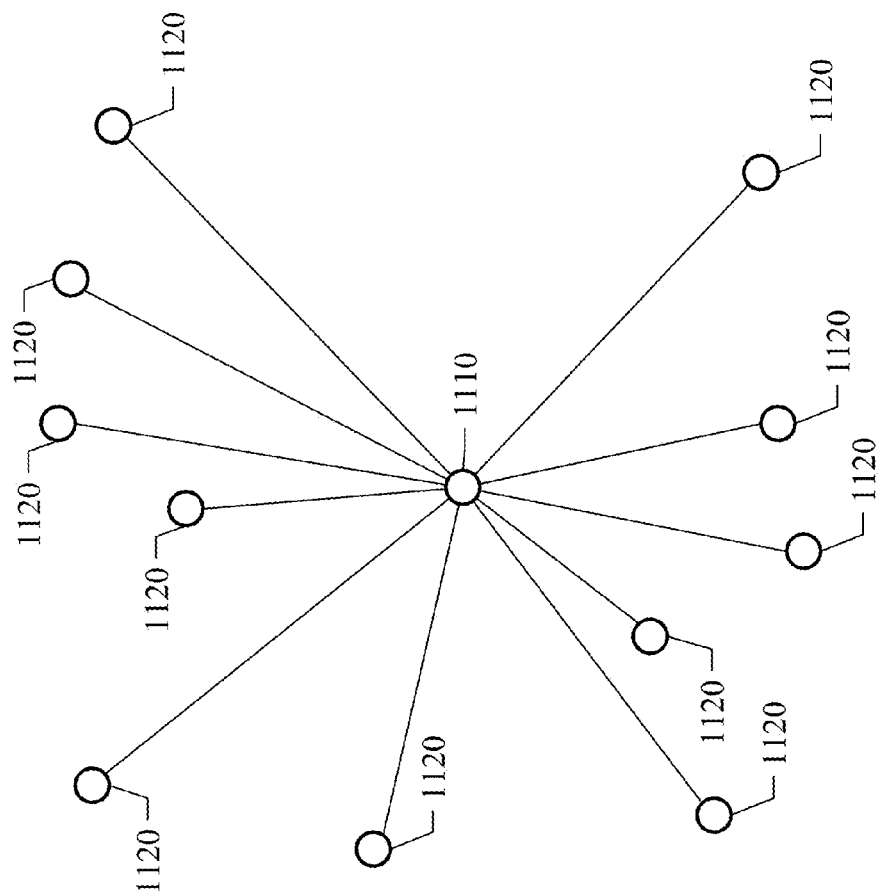
FIG. 11 illustrates an example embodiment of a physician-referral-network.

FIG. 11 illustrates an example embodiment of a physician-referral-network for matching-engine system 160. Node 1110 corresponding to a first physician is connected by a plurality of edges with a plurality of nodes 1120 corresponding to a plurality of second physicians. In particular embodiments, one edge may be used for referrals from the first physician to a second physician, and a separate edge may be used for referrals in the other direction, e.g. from the second physician back to the first physician. In particular embodiments, the same edge may be used for referrals in both directions. In particular embodiments, matching-engine system 160 may only maintain edges for physicians within the same geographic location, such as an MSA. As an example and not by way of limitation, a physician may refer a patient to another physician across the country. This may be because the referred physician is renowned as the best in the field, or because the patient is traveling or moving to the location of the other physician. Matching-engine system 160 may consider these types of referrals to be an outlier referral, and not include the referral in the physician-referral-network. In particular embodiments, matching-engine system 160 may record any and all referrals made between healthcare providers, regardless of location or specialties.

In particular embodiments, the physician-referral-network may be used to identify unnecessary referrals. As an example and not by way of limitation, a particular physician may have a habit of referring patients to another physician for tests which are unnecessary for the patient's condition or treatment. In particular embodiments, the referring physician may simply be inefficient in making the referral. In particular embodiments, the referring physician may be intentionally making unnecessary referrals to drive up claims. Matching-engine system 160 may be able to determine that a referral from a first physician to a second physician tends to result in very low performance scores for one or both physicians, indicating that the referral results in inefficient treatment. Matching-engine system 160 may also be able to identify whether a first physician is making a referral to a second physician who is below-average experience in the type of medical services that the referral comprises, particularly if compared to other physicians referred to by the first physician or the first physician's peers. In particular embodiments, matching-engine system 160 may use a threshold performance score or experience index for referred physicians with respect to a referring physician.

In particular embodiments, matching-engine system 160 may inform either the referring physician or referred physician, or both, that the referrals are inefficient. As an example and not by way of limitation, matching-engine system 160 may be able to inform a physician who always refers patients for a particular condition that the referral is unnecessary for treatment or is an inefficient use of resources. In particular embodiments, if a referring physician makes referrals to another physician with resulting performance scores below the threshold performance score, matching-engine system 160 may filter out that referring physician from a set of recommended physicians for users requesting treatment in the same base concept or specialization as the unnecessary referrals. As an example and not by way of limitation, a referring physician Dr. Grant may see patients with migraines and/or vertigo. Dr. Grant may refer his migraine patients to Dr. Sattler, and refer his vertigo patients to Dr. Harding. However, if the performance score for patients referred to Dr. Harding fall below a threshold score, indicating that the referral may be unnecessary, matching-engine system 160 may filter out Dr. Grant from the set of recommended physicians for users searching for vertigo treatments. If the performance scores for patients referred to Dr. Sattler remain above a threshold, matching-engine system 160 may keep recommending Dr. Grant for users looking for physicians to treat migraines.

Figure 12:
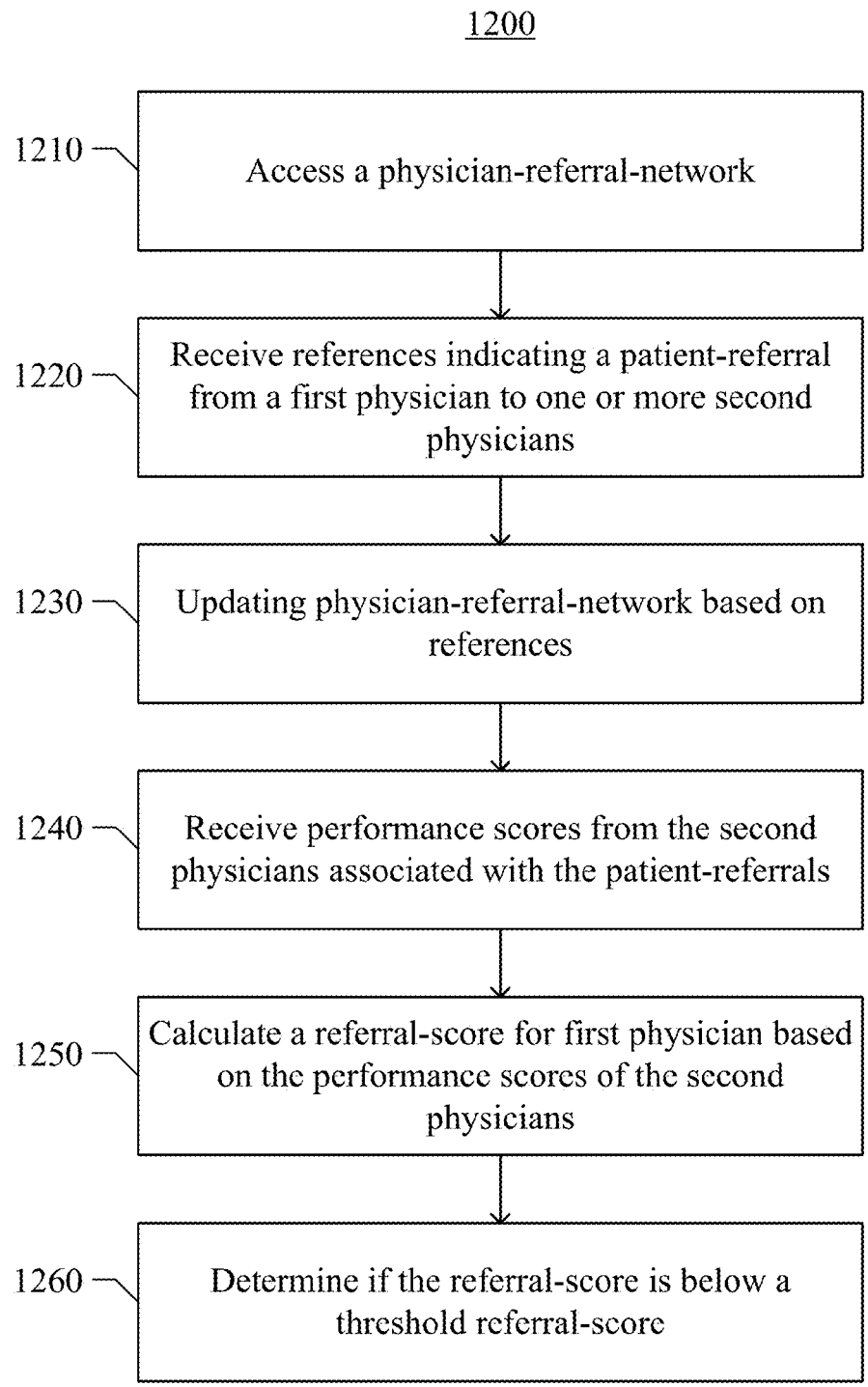
FIG. 12 illustrates an example method of updating a physician-referral-network.

FIG. 12 illustrates an example method for maintaining a record of patient referrals between physicians in a physician-referral-network. At step 1210, a physician-referral-network may be accessed by matching-engine system 160. At step 1220, matching-engine system 160 may receive a reference indicating a patient referral from a first physician to one or more second physicians. At step 1230, matching-engine system 160 may update the physician-referral-network based on the received reference. In particular embodiments, matching-engine system 160 may create a new edge connecting the nodes corresponding to the first physician and the second physicians. As an example and not by way of limitation, the first physician may be referring a patient to the second physician for the first time. In particular embodiments, an edge may already exist between the first physician and the second physicians. In this case, matching-engine system 160 may update the physician-referral-network to indicate that another referral has been made from the first physician to the second physician. At step 1240, matching-engine system 160 may receive performance scores from the second physicians, wherein the performance scores correspond to the patients referred to the second physicians by the first physician.

At step 1250, matching-engine system 160 may calculate a referral-score based at least in part on the received performance scores. In particular embodiments, the referral-score may be calculated by determining an average performance score for all the referrals from the first physician to the second physician. In particular embodiments, the average may be weighted based on the time of the referral, wherein recent referrals receive a higher weight than older referrals. In particular embodiments, the referral-score may be further based on the experience index of the second physicians, compared to a threshold experience index. In particular embodiments, the threshold experience index may be the average experience index of other physicians referred to by the first physician. In particular embodiments, the threshold experience index may be the average experience index of other physicians referred to by the first physician's peer group for similar conditions or treatments. At step 1260, matching-engine system 160 may determine if the referral-score is below a threshold referral-score. The threshold referral-score may be specified by an administrator or another user of matching-engine system 160, or may be determined by matching-engine system 160. As an example and not by way of limitation, the threshold referral-score may be the bottom 5% of all referral scores. If a particular referral-score is below the threshold, matching-engine system 160 may take further action, such as informing the first physician or the second physician, or by removing the first physician from the set of recommended physicians for one or more conditions or treatments.

Particular embodiments may repeat one or more steps of the method of FIG. 12, where appropriate. Although this disclosure describes and illustrates particular steps of the method of FIG. 12 as occurring in a particular order, this disclosure contemplates any suitable steps of the method of FIG. 12 occurring in any suitable order. Moreover, although this disclosure describes and illustrates particular components, devices, or systems carrying out particular steps of the method of FIG. 12, this disclosure contemplates any suitable combination of any suitable components, devices, or systems carrying out any suitable steps of the method of FIG. 12.

In particular embodiments, matching-engine system 160 may consider additional degrees of referrals made by physicians in calculating a referral-score. As an example and not by way of limitation, physician Dr. Grant may refer his patients with migraines to Dr. Sattler. Dr. Sattler may in turn refer some of those patients further to Dr. Malcolm. Matching-engine system 160 may calculate a referral-score for Dr. Sattler based on her referrals to Dr. Malcolm and any performance scores received as a result; additionally, Dr. Malcolm's performance scores or Dr. Sattler's referral-score for Dr. Malcolm for the migraine patients may be used as a factor in calculating the referral-score for Dr. Grant, the original referring physician. In particular embodiments, low performance scores by Dr. Malcolm with respect to Dr. Sattler may be reflected in Dr. Sattler's performance scores with respect to Dr. Grant. In particular embodiments, the additional step of performance scores and referral-scores may mask any inefficiencies at the end of the referral chain. As an example and not by way of limitation, Dr. Sattler may be extremely resource-efficient in her work, such that any inefficiencies from Dr. Malcolm do not carry through to any performance scores or referral-score from Dr. Grant's point of view. Therefore, it may be desirable for matching-engine system 160 to determine separately for Dr. Grant if any physician in a referral chain is inefficient. In particular embodiments, matching-engine system 160 may inform Dr. Grant that his referrals to Dr. Sattler result in inefficiencies further down the line.

Physician Scheduling System

Sending notifications to particular healthcare providers regarding potential patient appointments may cause a technical problem arising from the increased network connections and bandwidth required to send notifications to a large enough group of healthcare providers such that at least one response from a healthcare provider is likely. The embodiments described below may provide a technical solution to the problem described above by reducing the overall connections and bandwidth required for matching-engine system 160 or another suitable computing system to send notifications to healthcare providers by narrowing the overall number of notifications sent without reducing the likelihood that at least one of the healthcare providers will respond and schedule the patient appointment.

In particular embodiments, a user seeking medical advice or care may desire to visit a particular healthcare provider whose experience and prior performance is well-suited to the user or the exact nature of the medical advice or care the user is seeking. As an example and not by way of limitation, a user who is an active 25 year-old male who has chronic back pain may wish to see a doctor or other healthcare provider who has a high level of experience treating chronic back pain and in particular, experience in treating active males in the same age group as the user for chronic back pain. A healthcare provider with extensive experience compared to his peers in treating this patient group for that condition may be able to offer accurate and efficient diagnoses and therapies. Systems and methods for evaluating the experience of a healthcare provider is discussed in further detail in U.S. patent application Ser. No. 14/482,949, filed 10 Sep. 2014, which is incorporated herein by reference.

Similarly, a healthcare provider's prior performance in treating a particular patient group for a particular condition may be evaluated. In particular embodiments, a healthcare provider's performance may be scored as a measure of the resource cost incurred in treating a patient for a primary episode of care. Resource costs may be standardized across geographic regions (e.g., states, counties, cities, metropolitan statistical area, etc.) better than monetary costs. As an example and not by way of limitation, a particular therapeutic treatment may cost monetarily twice as much in region A as it does in region B; however, the resource cost may be the same in both regions. This may allow physicians in region A to be compared to physicians in region B based on the actual healthcare resources used. The performance score for a physician may reflect an indication of the amount of healthcare resources used by the physician or healthcare provider in delivery of care for treating patients with the same or similar clinical complexity. Complex treatments may result in more resources being consumed than simple cases regardless of physician skills, but there may be a variation in how much resources are used. As an example and not by way of limitation, a physician may have a better performance score because she is able to quickly diagnose the condition and follow a treatment path that is effective for the patient. As another example, a physician may have a lower performance score because he ordered additional tests before diagnosing a condition or ordered unnecessary or ineffective treatment options early on in the treatment process. Systems and methods for evaluating the performance of a healthcare provider is discussed in further detail in U.S. patent application Ser. No. 14/482,949, filed 10 Sep. 2014, which is incorporated herein by reference.

In particular embodiments, a user seeking medical care for diagnosis or treatment of a condition may send a query to a patient-provider-matching system for a search-results set of one or more physicians. The query may comprise a specific medical condition, one or more symptoms, one or more names of a medical specialty, a type of medical procedure, other suitable medical information, or any combination thereof. As an example and not by way of limitation, a user may send a query regarding physicians to treat plantar fasciitis. As another example and not by way of limitation, a user may send a query merely stating that the user has a headache and nausea, and request one or more physicians to help with the user's symptoms. As yet another example and not by way of limitation, a user may send a query for physicians able to perform a colonoscopy. In particular embodiments, a user may send separate queries for one or more symptoms, conditions, or treatments. In particular embodiments, a user may send a single query containing several distinct symptoms, conditions, or treatments. As an example and not by way of limitation, a user may submit a query that comprises an indication that the user needs an annual physical, and also that the user has stomach pains. A patient-provider-matching system may provide the user with a set of physicians for an annual physical, and a second set of physicians for the stomach pain. In particular embodiments, the patient-provider-matching system may send the user a single set of physicians, wherein the set comprises physicians for the annual physical and physicians for the stomach pain. In particular embodiments, there may be an overlap between the two different sets of physicians.

In particular embodiments, a patient-provider-matching system may determine a set of one or more physicians for a user to visit within a particular geographic region in which the user resides or works. In particular embodiments, the geographic region may be a metropolitan statistical area (MSA). MSAs are defined metropolitan regions determined by the United States Office of Management and Budget. As an example and not by way of limitation, a patient-provider-matching system may identify a set of physicians who are located within the Los Angeles-Long Beach-Anaheim MSA. In particular embodiments, a patient-provider-matching system may identify one or more physicians who are within a preset distance of the location of the user. As an example and not by way of limitation, the patient-provider-matching system may only identify physicians who are within 25 miles of the user. In particular embodiments, the user may specify a distance or region in which to look for physicians to recommend. As an example and not by way of limitation, a user may indicate that she only wants to view physicians within Orange County, Calif., without receiving recommendations for physicians within Los Angeles, Calif.

In particular embodiments, physicians in the determined set of physicians may be scored on a number of statistics in comparison to their peer group. As an example and not by way of limitation, matching-engine system 160 may determine a particular physician's 30-day readmissions rate, which is the rate at which patients treated by the particular physician are readmitted to a healthcare facility within 30 days of receiving treatment from the particular physician, as compared to the peer group. As another example and not by way of limitation, matching-engine system 160 may determine a rate of post-surgical infections or other post-treatment complications for the particular physician compared to the peer group. As yet another example and not by way of limitation, matching-engine system 160 may calculate an average length-of-stay for patients who are seen by the particular physician for a particular condition or treatment, compared to the average length-of-stay for the peer group. As yet another example and not by way of limitation, matching-engine system 160 may consider the relative invasiveness of procedures used by the particular physician, compared to the invasiveness of procedures used by the peer group of physicians. In particular embodiments, a patient may desire less invasive procedures if they are equally effective or even nearly as effective. In particular embodiments, matching-engine system 160 may also consider the ratings for the healthcare facility in which the particular physician practices. As an example and not by way of limitation, matching-engine system 160 may prioritize a physician practicing at a higher-rated facility since that may affect issues such as infection, readmission, length-of-stay, etc.

In particular embodiments, parameters for recommending one or more physicians to a user may be provided by an administrator of the particular user's health plan. As an example and not by way of limitation, if a user receives her health insurance coverage through her employment, and her employer has an administrator responsible for determining the healthcare coverage to be provided by the employer, then the administrator may specify an acceptable range of parameters within which to recommend physicians. As another example and not by way of limitation, the administrator may wish to specify a range of acceptable performance scores for physicians, acceptable monetary costs for physicians when conducting particular treatments or procedures, or an acceptable range of experience indices for physicians. In particular embodiments, performance score may represent a physician's efficiency in time and/or resources in treating a patient for a particular condition or disease, or in applying a particular treatment method. A performance score may be of interest to both a patient and the patient's insurance provider as an indication that a physician will require less time, office visits, resources, etc. In particular embodiments, an experience index for a physician may indicate the physician's experience in dealing with a particular condition or disease, or in performing a particular treatment method. In particular embodiments, the experience index may also represent how many different types of conditions within a condition group a physician has seen. These parameters may allow the administrator to direct users towards physicians that the administrator has determined are cost-effective physicians, or in the alternative, physicians that are above a threshold baseline of competency while remaining affordable for the employer. In particular embodiments, when a user of the healthcare plan run by that administrator submits a query for one or more physicians, a patient-provider-matching system may only present physicians meeting the acceptable parameters specified by the administrator. In particular embodiments, a patient-provider-matching system may include other physicians, but may rank the physicians meeting the administrator's parameters more highly. Systems and methods for matching medical providers and patients are discussed in further detail in U.S. patent application Ser. No. 14/482,921, filed 10 Sep. 2014, which is incorporated herein by reference.

In particular embodiments, matching-engine system 160 may include information related to the availability of a particular physician. As an example and not by way of limitation, matching-engine system 160 may have information from each physician indicating when they are next available to make a new appointment. As another example and not by way of limitation, matching-engine system 160 may estimate the next availability of each physician based on the current schedule of appointments for that physician. As yet another example and not by way of limitation, matching-engine system 160 may predict an availability of a particular physician based on historical data corresponding to previous patient appointments for similar conditions. For example, a particular physician may have general availability on Tuesday morning and Friday afternoon, for a patient seeking an appointment for consultation on a back surgery. However, if the data on previous patient appointments shows that the particular physician ordinarily does not conduct surgical consulting appointments in the mornings, matching-engine system 160 may indicate that the next available time is on Friday. In particular embodiments, matching-engine system 160 may use the date the physician is next available as a factor in selecting a matching set of physicians. In particular embodiments, matching-engine system 160 may prioritize physicians who have more recent availability. Prioritizing based on recent availability may be particularly useful if the patient is seeking an appointment for a condition or treatment that is more urgent. In particular embodiments, matching-engine system 160 may display the next availability of each physician in the determined set of physicians to the user, so that the user may see the availability and select one of the physicians to schedule an appointment.

In particular embodiments, each patient may be further grouped into one of a number of risk groups. In particular embodiments, a patient's "risk" may be a predictor of the medical resources that patient is likely to require based on information known about that patient. Grouping patients by risk may allow more detailed evaluation of healthcare provider experience and performance. As an example and not by way of limitation, Dr. Smith and Dr. Johnson, both orthopedic surgeons in the same geographic region, may each have seen a similar number of female, middle-aged patients for knee replacement surgery. If Dr. Smith's performance score for this patient demographic and treatment is superior to that of Dr. Johnson, an outside observer may think that Dr. Smith is more efficient at knee replacement surgery than Dr. Johnson. However, it may be that most of Dr. Smith's knee-replacement patients were otherwise healthy, while a significant number of Dr. Johnson's patients had other existing medical conditions, or comorbidities. These comorbidities may have required additional resources to be used during the surgery, which would reflect badly on Dr. Johnson's performance score. Therefore, many of Dr. Johnson's patients may be considered to be in a "high-risk" patient group, while most of Dr. Smith's patients were in a "low-risk" group. If the performance scores are further grouped by risk groups, Dr. Smith and Dr. Johnson may be found to be equal performers for each risk-group; but because Dr. Johnson treated a proportionally higher number of high-risk patients, her overall performance may appear to be lower.

As another example and not by way of limitation, patient risk groups may also be used to improve matching a particular patient to an appropriate healthcare provider. Continuing the example above, a middle-aged female patient in need of a knee replacement surgery may search for orthopedic surgeons in the area using a patient-provider-matching system. However, this patient has a number of comorbidities such as arthritis, diabetes, heart disease, and osteoporosis, which may require additional resources to be used during the knee replacement surgery. If the healthcare providers' performance and experience scores are not adjusted by patient risk groups, the patient-provider-matching system may recommend Dr. Smith to the patient because Dr. Smith has a better performance score compared to Dr. Johnson. However, if the performance and experience scores are grouped by the patients' respective risk groups, then the patient-provider-matching system may recommend Dr. Johnson, who has more experience treating "high-risk" patients, to this patient. Further discussion of patient risk and providing search results to a user based on the user's risk score is provided in U.S. patent application Ser. No. 15/079,567, filed 24 Mar. 2016, which is incorporated herein by reference.

In particular embodiments, a user may access matching-engine system 160 using a client system 130 associated with the user to search for a physician. As an example and not by way of limitation, a user may log onto a website of matching-engine system 160 and search for a physician to treat the user for a particular symptom or to receive a particular treatment. In particular embodiments, matching-engine system 160 may receive one or more search terms from the user, and perform a search for one or more physicians or healthcare providers who correspond to the search terms. In particular embodiments, the user may submit additional information to help filter the number of search results.

In particular embodiments, an entity operating matching-engine system 160 may operate a call center to receive and process patient appointments via telephone. The call center may use an automated directory system or an operator to receive telephone calls from potential patients who wish to schedule an appointment. As an example and not by way of limitation, a hospital or healthcare network may provide a telephone number for potential patients to call. An automated system may collect basic information from the potential patient, such as name, address, medical insurance, and whether the potential patient has previously visited the hospital or the healthcare network. In this example, the call may then be transferred to a human operator who may collect information regarding the purpose of the potential patient's call, and help the potential patient identify the type of healthcare services they desire and when they would like to schedule a patient appointment. In particular embodiments, matching-engine system 160 may receive the information provided by the potential patient and determine a set of matching physicians.

In particular embodiments, a user may call in to a call center or access a website associated with matching-engine system 160 to request a patient appointment with a physician. In particular embodiments, the call center or website may collect information about the user. The call center or website may collection information regarding the user's age, gender, or other demographic information; receive information about the request such as a symptom that the user has or a treatment or procedure that the user desires; the geographic location of the user; one or more times that the user desires to have the patient appointment, other suitable information, or any combination thereof. As an example and not by way of limitation, the user may specify that they would prefer an appointment on weekday mornings, or that they would prefer a weekend appointment if possible. In particular embodiments, based on the information provided about the user and the user's symptoms or treatments, matching-engine system 160 may determine one or more physicians who have a high matching score with the patient. As an example and not by way of limitation, matching-engine system 160 may determine a set of ten physicians who are geographically proximate to the user, and have at least a threshold experience score and performance score with respect to a condition or treatment associated with the user based on the collected information.

In particular embodiments, matching-engine system 160 may further have information related to the availability of each of the physicians in the determined set. As an example and not by way of limitation, the physicians may be subscribers of a physician scheduling service associated with matching-engine system 160. Each physician may identify to matching-engine system 160 a set of time periods during which they would be available to see patients that have been scheduled through matching-engine system 160. In particular embodiments, each of the physicians may also identify a set of time periods during which they are not available to receive patients. In particular embodiments, when matching-engine system 160 determines a set of physicians who correspond to the information collected from the patient, one or more of the physicians may be eliminated if the times specified by the patient do not correspond to any available time for the physician. In particular embodiments, the patient may specify a priority of preferred dates and times for an appointment. Matching-engine system 160 may identify physicians whose available times correspond to the preferred times, and rank those identified physicians higher than physicians who are available at times specified by the user, but not a preferred time.

In particular embodiments, matching-engine system 160 may not have access to information regarding the availability of the determined set of physicians. As an example and not by way of limitation, one or more of the determined set of physicians may not subscribe to a scheduling service associated with matching-engine system 160. As another example, one or more of the determined set of physicians may have neglected to provide any information regarding their availability in the current week or month. In particular embodiments, multiple physicians may have availability at the preferred date and time, or the availability of multiple physicians may be unknown. In particular embodiments, matching-engine system 160 may instead send a notification to each of the set of physicians notifying them of a potential patient appointment. In particular embodiments, the notification system may resemble a real-time bidding system, wherein the notified physicians can respond to the notification in order to schedule an appointment with that patient. In particular embodiments, a notification may be pushed out to a computing device associated with each physician. As an example and not by way of limitation, a notification may be sent by e-mail; automated phone call; SMS message, instant message, telephone message, fax, or any other reasonable means of contacting the physician. In particular embodiments, the notification may be sent by a server associated with matching-engine system 160 which is configured to push notifications to a set of recipients as determined by matching-engine system 160. In particular embodiments, each physician may identify a preferred method of receiving notifications, or a priority of notification methods. As an example and not by way of limitation, a physician may indicate that he wishes to receive notifications via SMS message, with a backup option of e-mail should SMS messaging be unavailable for the physician's mobile device in certain locations or times. In particular embodiments, a physician may subscribe to a notification service associated with matching-engine system 160 in order to receive notifications of potential patient appointments. Physicians may not pay any fees to subscribe to this service. In particular embodiments, the subscription may require that physicians provide additional information to matching-engine system 160. As an example and not by way of limitation, physicians may provide information regarding preferred methods of notification, preferred times to receive notifications, preferred times of appointments, the insurance providers the physician accepts, or what type of patients or conditions/treatments the physician would like notifications about through this service.

In particular embodiments, the notification to a particular physician may be made to an automated scheduling system for the physician. As an example and not by way of limitation, a particular physician may have set an online service or other computing system to automatically accept or decline appointments. In particular embodiments, the notification may be sent to the automated system of the physician, which may provide either an acceptance or a decline in response. In particular embodiments, whether the automated system sends an acceptance or a decline may be based on information available to the automated system, but not matching-engine system 160. As an example and not by way of limitation, the automated system may send a response based on an updated schedule of the physician, any additional personal preferences of the physician for scheduling appointments, or any other information that would affect the physician's likelihood of accepting or declining an appointment.

In particular embodiments, matching-engine system 160 may send notifications to all of the physicians in the determined set. In particular embodiments, the first of the physicians to respond positively to the notification may be assigned the patient appointment. As an example and not by way of limitation, matching-engine system 160 may send notifications to a set of physicians via SMS message and instant message, with the first physician to respond to the SMS message or instant message with an acceptance of the patient appointment. In particular embodiments, upon receiving the acceptance response back from a physician, matching-engine system 160 may contact the patient to inform them of the appointment with the responsive physician. In particular embodiments, matching-engine system 160 may also send a notification to the physician who sent the acceptance response, informing them of the now-scheduled appointment with the patient. In particular embodiments, matching-engine system 160 may send a second notification to the other physicians who received the original notification, indicating that the appointment has already been filled. In particular embodiments, a physician may alternatively send a decline of the patient appointment in response to the notification, indicating that they would prefer not to book the appointment. As an example and not by way of limitation, if a physician's schedule indicated that they were available at a particular time, but subsequently after updating the schedule, but before the notification was sent, the physician's plans changed, the physician may no longer be available at that time. The physician may then send a decline of the appointment. In particular embodiments, matching-engine system 160 may update the physician's schedule to indicate that the physician is no longer available at the requested date and time in response to receiving a decline.

In particular embodiments, matching-engine system 160 may prioritize a subset of the determined set of physicians to first send notifications to. In particular embodiments, if none of the physicians in the subset sends an acceptance in response to the notification within a predetermined time period, matching-engine system 160 may then send notifications to one or more other physicians in the determined set. In particular embodiments, matching-engine system 160 may require physicians to affirmatively respond negatively (e.g., with a decline) before determining that the physician does not wish to take the offered appointment. In particular embodiments, matching-engine system 160 may use a default waiting period (e.g. 30 minutes) and determine that a lack of response by a particular physician within the waiting period corresponds to a decline response. In particular embodiments, several physicians, or their automated scheduling systems, may send an acceptance in response to a particular notification within a short period of time. In particular embodiments, the acceptance responses may be received before a second notification informing the physicians that the appointment has been taken has been sent. In particular embodiments, matching-engine system 160 may still assign the appointment to the first physician who responded. Matching-engine system 160 may then determine that the other physicians who send the acceptance responses may receive a greater priority for a future notification for a similar patient appointment.

In particular embodiments, matching-engine system 160 may use a set of filters provided by each individual physician to determine whether the physician should receive a notification regarding a particular patient appointment. As an example and not by way of limitation, a particular physician may indicate that they would prefer patients with medical insurance from ABC Co., and that while the physician would take a patient with insurance from XYZ Co., those patients would be less desirable. Another physician may indicate that she would only like to make consulting appointments through matching-engine system 160 for a limited set of conditions or treatments, even though she is qualified in other conditions or treatments.

In particular embodiments, the filters specified by each physician may specify a range of desirable risk scores associated with a patient. As an example and not by way of limitation, a physician who is an orthopedic surgeon with experience in knee replacement surgeries may have a lot of previous experience successfully performing surgeries on patients with high risk scores, i.e. a higher likelihood of requiring additional healthcare resources. That physician may indicate that he or she wishes to continue receiving patients who have high risk scores and are seeking knee replacement surgery. A second orthopedic surgeon may have relatively little experience performing knee replacement surgeries on high-risk-score patients. Therefore, the second physician may indicate that he or she would prefer to see patients with lower risk scores for knee replacement surgeries.

In particular embodiments, matching-engine system 160 may attempt to distribute notifications of potential patient appointments in a load-balancing scheme. As an example and not by way of limitation, a potential patient Alice may call into the call center of matching-engine system 160 requesting an appointment to see a physician for hip pain on the following Friday in the morning. Matching-engine system 160 may determine a matching set of physicians Drs. Carson, Darby, Easton, Frank, Goldberg, and Hu, and send notifications to the first three: Carson, Darby and Easton. Upon receiving a response from Dr. Easton that she is available, matching-engine system 160 may schedule an appointment for Alice to see Dr. Easton. The next day, potential patient Irene may log onto the website of matching-engine system 160 seeking an appointment for her hip pain, and request an appointment for the following Friday in the afternoon. Matching-engine system 160 may again determine a matching set of physicians, the same set of physicians as the list above. However, since the first set of notifications (for Alice) were sent to Drs. Carson, Darby and Easton, matching-engine system 160 may determine that the notifications regarding Irene may be sent to the other physicians, Drs. Frank, Goldberg, and Hu.

In particular embodiments, matching-engine system 160 may send additional notifications to a set of physicians, but omitting one or more physicians who were recently matched for the same type of appointment. As an example and not by way of limitation, in the example above, for a potential appointment for Irene, matching-engine system 160 may determine that all of the physicians should receive a notification except Dr. Easton, who already has an appointment scheduled with Alice. In this example, if Dr. Hu subsequently responds that he can see Irene for her appointment, and subsequently there is a third patient requesting an appointment, matching-engine system 160 may omit both Dr. Easton and Dr. Hu from the notification for that third appointment.

In particular embodiments, matching-engine system 160 may use statistics related to physician responses to previous notifications as a factor in determining a subset of physicians to notify. As an example and not by way of limitation, if a physician has a low rate of responding to received notifications, matching-engine system 160 may assign a lower priority to that physician in the future, meaning that other physicians (with higher response rates) will receive notifications first. In particular embodiments, the response rate may only consider the number of positive responses (e.g., "yes" messages) sent by the physician. In particular embodiments, the response rate may include negative responses (e.g., "no" messages) as well, so that physicians who actively respond to the notifications with any sort of response receive higher priority. In particular embodiments, the response rate may consider the actual rate of appointments made. As an example and not by way of limitation, matching-engine system 160 may penalize physicians who agree to the patient appointments sent by matching-engine system 160, but then later cancel or reschedule those appointments.

Figure 13:
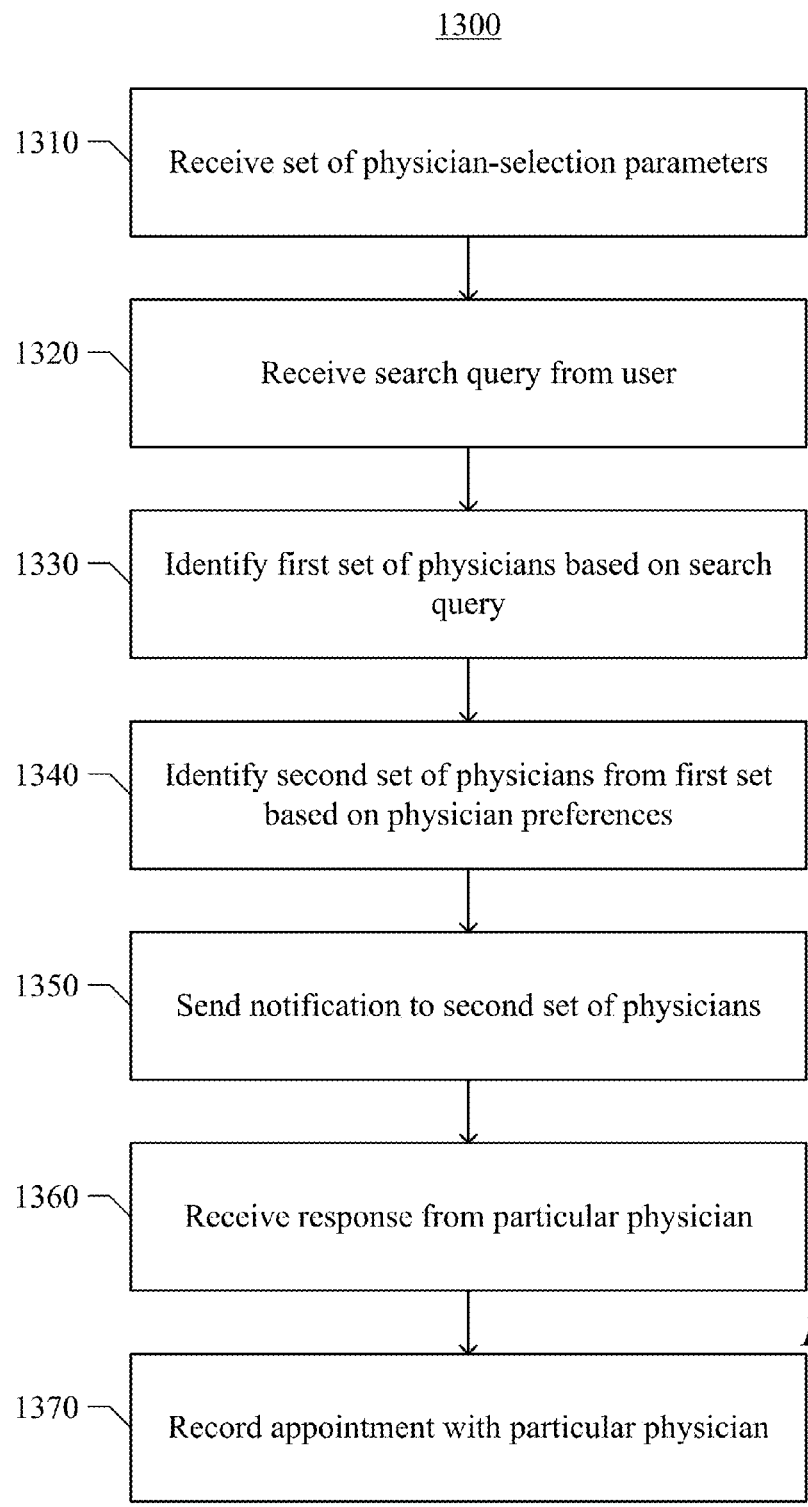
FIG. 13 illustrates an example method of notifying physicians of a potential appointment.

FIG. 13 illustrates an example method for scheduling an appointment with a physician through a bidding system. The method may start at step 1310, where matching-engine system 160 may receive from an administrator a set of parameters. In particular embodiments, the set of parameters may comprise a range of acceptable performance scores, a range of acceptable experience indices, or a range of acceptable costs. In particular embodiments, matching-engine system 160 may store the set of parameters in a database, associating the set of parameters with a group of one or more users corresponding to the administrator. As an example and not by way of limitation, the group of users may comprise the employees on an employer-provided health-care plan.

At step 1320, matching-engine system 160 may receive a search query from a user of matching-engine system 160. In particular embodiments, the search query comprises a geographic location of the user, a preferred date and time for an appointment, and one or more user-specified symptoms or a user-specified treatment. In particular embodiments, matching-engine system 160 may further determine one or more base-concepts based on the user-specified symptoms or a user-specified treatment of the search query. In particular embodiments, the base-concepts refer to a medical diagnosis or a medical procedure.

At step 1330, matching-engine system 160 may identify a first set of physicians based on the search query. In particular embodiments, identification of the physicians in the first set is based on the respective geographic location of each physician compared to the geographic location of the user. In particular embodiments, identification of the physicians is further based on a performance-score and an experience-score of the physician with respect to the particular base-concepts associated with the search query. As an example and not by way of limitation, matching-engine system 160 may select physicians for inclusion in the first set who have performance-scores and/or experience-scores above the acceptable indices indicated by the administrator.

At step 1340, matching-engine system 160 may identify a second set of physicians from the first set of physicians. In particular embodiments, the second set of physicians is a subset of the first set. In particular embodiments, identification of the second set of physicians is based on one or more physician preferences of each physician, and whether the physician has indicated availability at the preferred date and time of the search query. In particular embodiments, identification of the second set of physicians may also be based on a priority score associated with the physicians. The priority score may be based on factors such as the response rate of the physicians, and whether they have recently received prior notifications. In particular embodiments, the response rate may be based on the number of "yes" responses a physician has sent in response to a notification. In particular embodiments, the response rate may also include affirmative "no" responses to a notification indicating that the particular physician is unable to take that appointment. In particular embodiments, the response rate may also include the rate at which appointments were completed by the particular physician. As an example and not by way of limitation, if a particular physician had a high acceptance rate to notifications, but subsequently cancelled a high number of those appointments, matching-engine system 160 may lower the response rate for that physician to the number of completed appointments per notification sent. In particular embodiments, the one or more physician parameters may include an insurance provider that the physician accepts, or a risk score of the user that the physician is willing to accept.

At step 1350, matching-engine system 160 may send a notification to each of the second set of physicians. At step 1360, a particular physician may send a response to the notification to matching-engine system 160. In particular embodiments, the response may be a decline of the appointment, or an acceptance of the appointment.

At step 1370, matching-engine system 160 records the appointment between the particular physician and the user for the preferred date and time. In particular embodiments, once the appointment is recorded, another notification may be sent to the other physicians in the second set indicating that the appointment has been filed. As an example and not by way of limitation, the second set of physicians may comprise Dr. Murray, Dr. Nichols, and Dr. O'Brien, each of whom receives a notification for a particular user at a particular date and time. Dr. Nichols may be the first to respond, and the appointment is booked for her. In addition to recording the appointment, matching-engine system 160 may further send another notification to Drs. Murray and O'Brien informing them that the patient has been scheduled for an appointment.

In particular embodiments, multiple physicians may send a response at step 1360 to matching-engine system 160. In such a case, matching-engine system 160 may assign the appointment to the physician who was first in time, and notify the other physicians that their response was late. In particular embodiments, matching-engine system 160 may increase the priority score for the late-responding physicians to improve the likelihood that they may be identified into the second set of physicians for a future search query. As an example and not by way of limitation, in the example above, if Dr. O'Brien sent his response five seconds after Dr. Nichols, matching-engine system 160 may determine that the appointment still goes to Dr. Nichols, but may increase the priority score for Dr. O'Brien so that he is more likely to be selected in a future search query.

In particular embodiments, matching-engine system 160 may determine that no physician from the second set has sent an affirmative response to the notification in order to set an appointment. As an example and not by way of limitation, matching-engine system 160 may send notifications to Drs. Alice, Bob, and Charlie for a particular search query. Alice and Bob may send affirmative "no" responses indicating that they are unable to take the appointment, and Charlie may not respond within a predetermined response period, such as an hour. In this case, matching-engine system 160 may select a third set of physicians drawn from the first set of physicians, but no physician from the second set may be included in the third set. As an example and not by way of limitation, continuing the example above, after determining that no appointment could be made with Alice, Bob, or Charlie, matching-engine system 160 may identify a third set of Drs. David, Esther, and Frank, and send notifications to those physicians. If at least one of the third set of physicians responds in the positive, an appointment may be set for that physician. If matching-engine system 160 determines that none of the third set have responded affirmatively, matching-engine system 160 may select another set of physicians from the first set, excluding those physicians from the second and third sets. In particular embodiments, this process may be repeated until a physician responds in the affirmative.

Particular embodiments may repeat one or more steps of the method of FIG. 13, where appropriate. Although this disclosure describes and illustrates particular steps of the method of FIG. 13 as occurring in a particular order, this disclosure contemplates any suitable steps of the method of FIG. 13 occurring in any suitable order. Moreover, although this disclosure describes and illustrates particular components, devices, or systems carrying out particular steps of the method of FIG. 13, this disclosure contemplates any suitable combination of any suitable components, devices, or systems carrying out any suitable steps of the method of FIG. 13.

Figure 14:
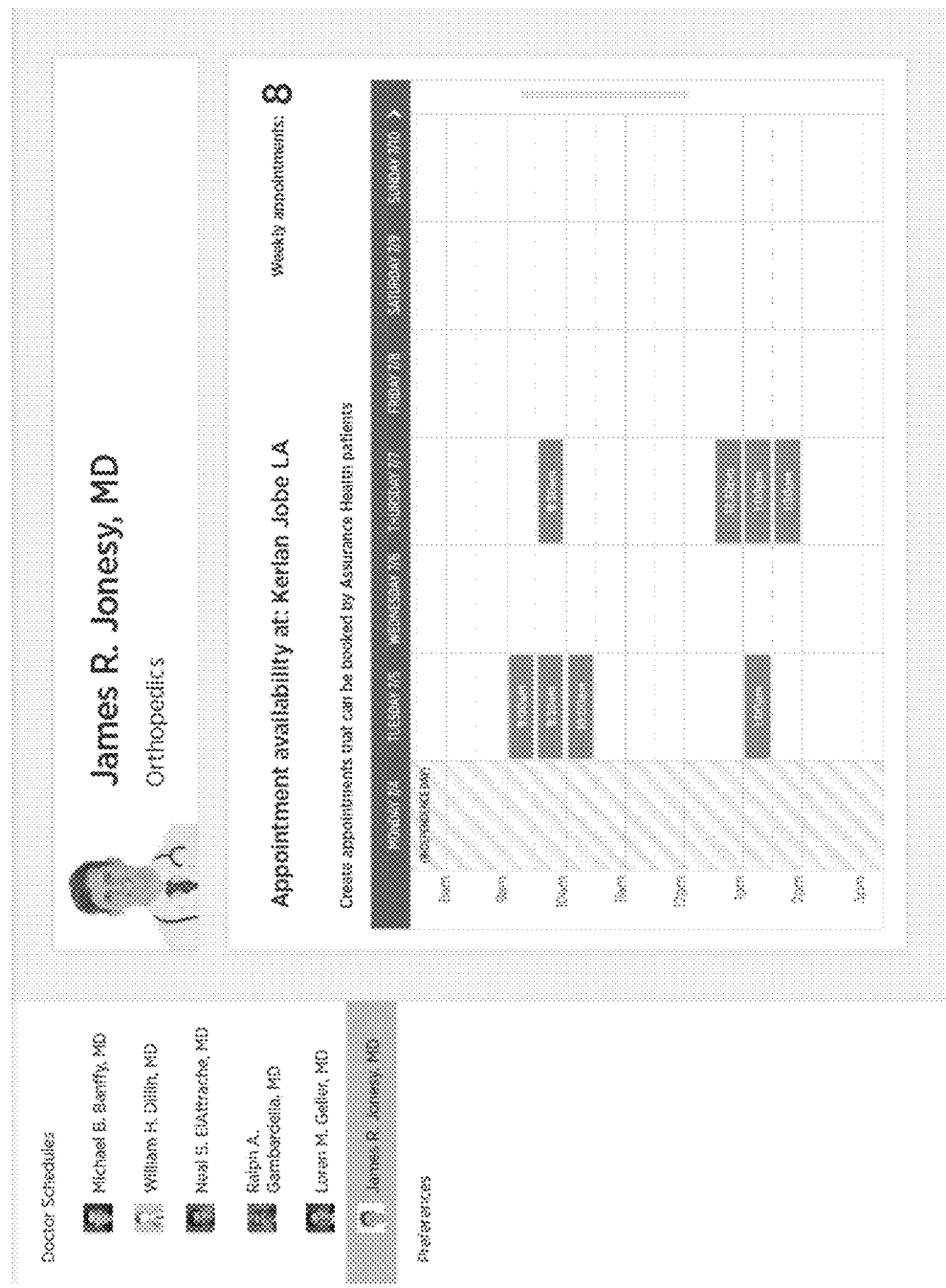
FIG. 14 illustrates an example illustration of a schedule of availability for a particular physician.

FIG. 14 illustrates an example embodiment of an availability of a particular physician during a particular time period. In this example, a particular physician may have indicated a number of times at which he is able to see patients for appointments. The particular physician may have a number of time slots on particular days on which the physician has set as available. In particular embodiments, for the times that do not have an available slot, matching-engine system 160 may determine that a notification should still be sent to the physician, in case the physician is willing to accept patients outside the designated times. In particular embodiments, matching-engine system 160 may determine that the physician should not be notified if a patient has requested a date and time outside the designated available times. In particular embodiments, matching-engine system 160 may default to a notification setting for undesignated times, and the individual physicians may alter those settings. In particular embodiments, the physician may affirmatively add particular time slots during which he may be absolutely unavailable to see patients. As an example and not by way of limitation, if a physician is also giving a lecture course from 3-5 p.m. on Thursdays, the physician may specify that no notifications should ever be sent for user requests within that time frame.

Privacy

In particular embodiments, one or more of the data objects of the online healthcare provider search engine may be associated with a privacy setting. The privacy settings (or "access settings") for an object may be stored in any suitable manner, such as, for example, in association with the object, in an index on an authorization server, in another suitable manner, or any combination thereof. A privacy setting of an object may specify how the object (or particular information associated with an object) can be accessed (e.g., viewed or shared) using the online healthcare provider search engine. Where the privacy settings for an object allow a particular user to access that object, the object may be described as being "visible" with respect to that user. As an example and not by way of limitation, a user of the online healthcare provider search engine may specify privacy settings for a user-profile page identify a set of users that may access the work experience information on the user-profile page, thus excluding other users from accessing the information. In particular embodiments, the privacy settings may specify a "blocked list" of users that should not be allowed to access certain information associated with the object. In other words, the blocked list may specify one or more users or entities for which an object is not visible. As an example and not by way of limitation, a user may specify a set of users that may not access photos albums associated with the user, thus excluding those users from accessing the photo albums (while also possibly allowing certain users not within the set of users to access the photo albums). In particular embodiments, privacy settings may be associated with particular patient information. Privacy settings may specify how one or more items of patient information can be accessed using the online healthcare provider search engine. In particular embodiments, privacy settings may allow users to opt in or opt out of having their actions logged by matching-engine system 160 or shared with other systems (e.g., third-party system 170). In particular embodiments, the privacy settings associated with an object may specify any suitable granularity of permitted access or denial of access. As an example and not by way of limitation, access or denial of access may be specified for particular users, user groups, user networks, all users ("public"), no users ("private"), users of third-party systems 170, particular applications (e.g., third-party applications, external websites), other suitable users or entities, or any combination thereof. Although this disclosure describes using particular privacy settings in a particular manner, this disclosure contemplates using any suitable privacy settings in any suitable manner.

In particular embodiments, one or more servers 162 may be authorization/privacy servers for enforcing privacy settings. In response to a request from a user (or other entity) for a particular object stored in a data store 164, matching-engine system 160 may send a request to the data store 164 for the object. The request may identify the user associated with the request and may only be sent to the user (or a client system 130 of the user) if the authorization server determines that the user is authorized to access the object based on the privacy settings associated with the object. If the requesting user is not authorized to access the object, the authorization server may prevent the requested object from being retrieved from the data store 164, or may prevent the requested object from be sent to the user. Although this disclosure describes enforcing privacy settings in a particular manner, this disclosure contemplates enforcing privacy settings in any suitable manner.

Miscellaneous

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, feature, functions, operations, or steps, any of these embodiments may include any combination or permutation of any of the components, elements, features, functions, operations, or steps described or illustrated anywhere herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative.

What is claimed is:

1. A method comprising:
   receiving, by one or more computing devices of a matching-engine system, from an administrator of the matching-engine system a set of physician-selection parameters comprising:
      a range of acceptable performance-scores for physicians; and
      a range of acceptable experience-scores for physicians;
   receiving, by the one or more computing devices, a search query from a client device of a user of the matching-engine system, wherein the search query comprises:
      a geographic location of the user;
      a preferred date and time for an appointment; and
      one or more of a user-specified symptom or a user-specified treatment;
   determining, by the one or more computing devices, at least one base-concept based on the search query, the base-concept comprising a medical diagnosis or a medical procedure;
   identifying, by the one or more computing devices, a first set of physicians from a plurality of physicians, wherein identifying each physician from the first set is based at least in part on:
      a geographic location of the physician;
      a performance-score associated with the physician with respect to the at least one base-concept, wherein the performance-score is calculated based on a weighted aggregate of individual performance-scores for one or more sub-concepts of the base-concept, wherein the individual performance-scores are calculated by:
         (1) accessing one or more Current Procedural Terminology (CPT) codes from claims data received from the physician, wherein the CPT codes refer to a medical service provided by the physician in connection with the one or more sub-concepts;
         (2) determining one or more relative value units (RVUs) corresponding to the one or more CPT codes, wherein the RVUs corresponding to a CPT code represents a location-independent measure of overall resources used for the medical service;

(3) calculating a physician-cost-factor for the physician associated with the one or more sub-concepts, wherein the physician-cost-factor is based on the RVUs corresponding to the medical service provided by the physician for the one or more sub-concepts;

(4) accessing an average cost factor associated with the one or more sub-concepts for a plurality of physicians, wherein the physician and the plurality of physicians share a common specialty and common geographic location; and (5) comparing the physician-cost-factor with the average cost factor, wherein the individual performance-score for the physician for the one or more sub-concepts is increased if the physician-cost-factor is lower than the average cost factor;

an experience-score associated with the physician with respect to the at least one base-concept; and the physician-selection parameters;

identifying, by the one or more computing devices, a second set of physicians, the second set being a subset of the first set, wherein the identification of each physician in the second set is based at least in part on:
one or more physician preferences; and
an availability of the physician with respect to the preferred date and time;

sending, by the one or more computing devices, a notification to each of the second set of physicians, the notification comprising information referencing the base-concept and the preferred date and time;

receiving, by the one or more computing devices, an indication responsive to the notification from a particular physician from the second set of physicians, the indication comprising an acceptance of an appointment for the user at the preferred date and time; and recording, by the one or more computing devices, an appointment for the user with the particular physician at the preferred date and time.

2. The method of claim 1, further comprising:
in response to recording the appointment with the particular physician, sending a notification to each other physicians in the second set of physicians that the user has scheduled an appointment.

3. The method of claim 1, wherein identification of the second set of physicians is further based on a priority score associated with each physician.

4. The method of claim 3, wherein the priority score for each physician is based on a response rate of the physician to previous notifications sent to the physician.

5. The method of claim 4, wherein the response rate is based on a number of acceptances of appointments responsive to notifications sent to the physician.

6. The method of claim 5, wherein the indication responsive to the notification may further comprise a decline of the appointment, and the response rate is further based on a number of declines of appointments responsive to notifications sent to the physician.

7. The method of claim 4, wherein the response rate is based on a number of previous appointments completed by the physician with respect to the number of previous acceptances of appointments responsive to notifications sent to the physician.

8. The method of claim 3, further comprising:
determining that indications from a plurality of physicians accepting the appointment have been received responsive to the notifications; and selecting one of the physicians from the plurality of physicians, wherein:
the appointment is recorded for the selected physician; and
the indication from the selected physician was received earlier than the other indications from the plurality of physicians.

9. The method of claim 4, further comprising, for each of the plurality of physicians accepting the appointment who are not the selected physician, increasing the priority score associated with each physician.

10. The method of claim 3, wherein the priority score for each physician is based on a number of previous notifications sent to the physician.

11. The method of claim 3, wherein the priority score for each physician is based on determining that the physician is a subscriber to a notification service associated with the matching-engine system.

12. The method of claim 1, wherein:
the search query further comprises an indication of an insurance provider of the user; and
the one or more physician parameters comprises a preference for one or more insurance providers.

13. The method of claim 1, wherein:
the search query further comprises a patient risk-score associated with the user; and
the one or more physician parameters comprises a preference for patients in a particular risk-score group.

14. The method of claim 1 wherein the common geographic location comprises:
a metropolitan statistical area; or
a geographic location defined by the user.

15. The method of claim 1, wherein the notification further comprises information referencing the user.

16. One or more computer-readable non-transitory storage media embodying software that is operable when executed to:
receive from an administrator a set of physician-selection parameters comprising:
a range of acceptable performance-scores for physicians; and
a range of acceptable experience-scores for physicians;
receive a search query from a client device of a user, wherein the search query comprises:
a geographic location of the user;
a preferred date and time for an appointment; and
one or more of a user-specified symptom or a user-specified treatment;
determine at least one base-concept based on the search query, the base-concept comprising a medical diagnosis or a medical procedure;
identify a first set of physicians from a plurality of physicians, wherein identifying each physician from the first set is based at least in part on:
a geographic location of the physician;
a performance-score associated with the physician with respect to the at least one base-concept, wherein the performance-score is calculated based on a weighted aggregate of individual performance-scores for one or more sub-concepts of the base-concept, wherein the individual performance-scores are calculated by:
(1) accessing one or more Current Procedural Terminology (CPT) codes from claims data received from the physician, wherein the CPT codes refer to a medical service provided by the physician in connection with the one or more sub-concepts;

(2) determining one or more relative value units (RVUs) corresponding to the one or more CPT codes, wherein the RVUs corresponding to a CPT code represents a location-independent measure of overall resources used for the medical service;
(3) calculating a physician-cost-factor for the physician associated with the one or more sub-concepts, wherein the physician-cost-factor is based on the RVUs corresponding to the medical service provided by the physician for the one or more sub-concepts;
(4) accessing an average cost factor associated with the one or more sub-concepts for a plurality of physicians, wherein the physician and the plurality of physicians share a common specialty and common geographic location; and
(5) comparing the physician-cost-factor with the average cost factor, wherein the individual performance-score for the physician for the one or more sub-concepts is increased if the physician-cost-factor is lower than the average cost factor;

an experience-score associated with the physician with respect to the at least one base-concept; and the physician-selection parameters;

identify a second set of physicians, the second set being a subset of the first set, wherein the identification of each physician in the second set is based at least in part on:
one or more physician preferences; and
an availability of the physician with respect to the preferred date and time;

send a notification to each of the second set of physicians, the notification comprising information referencing the base-concept and the preferred date and time;

receive an indication responsive to the notification from a particular physician from the second set of physicians, the indication comprising an acceptance of an appointment for the user at the preferred date and time; and record an appointment for the user with the particular physician at the preferred date and time.

17. A system comprising:
one or more processors; and
a memory coupled to the processors comprising instructions executable by the processors, the processors being operable when executing the instructions to:
receive from an administrator a set of physician-selection parameters comprising:
a range of acceptable performance-scores for physicians; and
a range of acceptable experience-scores for physicians;
receive a search query from a client device of a user, wherein the search query comprises:
a geographic location of the user;
a preferred date and time for an appointment; and
one or more of a user-specified symptom or a user-specified treatment;
determine at least one base-concept based on the search query, the base-concept comprising a medical diagnosis or a medical procedure;
identify a first set of physicians from a plurality of physicians, wherein identifying each physician from the first set is based at least in part on:
a geographic location of the physician;
a performance-score associated with the physician with respect to the at least one base-concept, wherein the performance-score is calculated based o a weighted aggregate of individual performance-scores for one or more sub-concepts of the base-concept, wherein the individual performance-scores are calculated by:
(1) accessing one or more Current Procedural Terminology (CPT) codes from claims data received from the physician, wherein the CPT codes refer to a medical service provided by the physician in connection with the one or more sub-concepts;
(2) determining one or more relative value units (RVUs) corresponding to the one or more CPT codes, wherein the RVUs corresponding to a CPT code represents a location-independent measure of overall resources used for the medical service;
(3) calculating a physician-cost-factor for the physician associated with the one or more sub-concepts, wherein the physician-cost-factor is based on the RVUs corresponding to the medical service provided by the physician for the one or more sub-concepts;
(4) accessing an average cost factor associated with the one or more sub-concepts for a plurality of physicians, wherein the physician and the plurality of physicians share a common specialty and common geographic location; and
(5) comparing the physician-cost-factor with the average cost factor, wherein the individual performance-score for the physician for the one or more sub-concepts is increased if the physician-cost-factor is lower than the average cost factor;

an experience-score associated with the physician with respect to the at least one base-concept; and the physician-selection parameters;

identify a second set of physicians, the second set being a subset of the first set, wherein the identification of each physician in the second set is based at least in part on:
one or more physician preferences; and
an availability of the physician with respect to the preferred date and time;

send a notification to each of the second set of physicians, the notification comprising information referencing the base-concept and the preferred date and time;

receive an indication responsive to the notification from a particular physician from the second set of physicians, the indication comprising an acceptance of an appointment for the user at the preferred date and time; and record an appointment for the user with the particular physician at the preferred date and time.

* * * * *